US012686706B2

(12) United States Patent
Johansson

(10) Patent No.: US 12,686,706 B2
(45) Date of Patent: Jul. 21, 2026

(54) COMPOUND AND METHOD FOR TREATMENT OF ALZHEIMER'S DISEASE

(71) Applicant: ALPHABETA AB, Djursholm (SE)

(72) Inventor: Jan Johansson, Stockholm (SE)

(73) Assignee: ALPHABETA AB, Djursholm (SE)

( * ) Notice: Subject to any disclaimer, the term of this patent is extended or adjusted under 35 U.S.C. 154(b) by 1020 days.

(21) Appl. No.: 17/784,591

(22) PCT Filed: Jan. 7, 2021

(86) PCT No.: PCT/EP2021/050168
§ 371 (c)(1),
(2) Date: Jun. 10, 2022

(87) PCT Pub. No.: WO2021/140140
PCT Pub. Date: Jul. 15, 2021

(65) Prior Publication Data
US 2023/0002458 A1      Jan. 5, 2023

(30) Foreign Application Priority Data

Jan. 8, 2020    (EP) ..................................... 20150738

(51) Int. Cl.
| | |
|---|---|
| *C07K 14/47* | (2006.01) |
| *A61K 38/00* | (2006.01) |
| *A61P 25/28* | (2006.01) |

(52) U.S. Cl.
CPC .............. *C07K 14/47* (2013.01); *A61P 25/28* (2018.01); *A61K 38/00* (2013.01)

(58) Field of Classification Search
None
See application file for complete search history.

(56) References Cited

FOREIGN PATENT DOCUMENTS

| | | |
|---|---|---|
| WO | WO 2011/162655 A1 | 12/2011 |
| WO | WO 2012/138284 A1 | 10/2012 |

OTHER PUBLICATIONS

Chen et al., "Bri2 BRICHOS client specificity and chaperone activity are governed by assembly state", Nature Communication, 2017, 8:2081, 14 pages.
Chen et al., "Augmentation of Bri2 molecular chaperone activity against amyloid-β reduces neurotoxicity in mouse hippocampus in vitro", Communications Biology, Jan. 2020, 3(1): 32, 12 pages.
Cheng et al., "Draft Genome and Complete Hox-Cluster Characterization of the Sterlet (*Acipenser ruthenus*)", Frontiers in Genetics, 2019, 10:776, 8 pages.
Database UniProt [Online], Wei, Q.: "Draft Genome and Complete Hox-Cluster Characterization of the SterletRT Sturgeon (*Acipenser ruthenus*).", XP002798719, Database accession No. A0A444U9X2, May 2019.
Database Protein [Online], Ncbi: "integral membrane protein 2B [Erpetoichthys calabaricus]", XP002798720, retrieved from NCBI Database accession No. XP_028655526, Apr. 2019.
Sanchez-Pulido et al., "BRICHOS: a conserved domain in proteins associated with dementia, respiratory distress and cancer", Trends in Biochemical Sciences, 2002, 27(7): 329-332.
Willander et al., "BRICHOS Domains Efficiently Delay Fibrillation of Amyloid β-Peptide", The Journal of Biological Chemistry, 2012, 287(37): 31608-31617.

*Primary Examiner* — Sergio Coffa
(74) *Attorney, Agent, or Firm* — James S. Keddie; Bozicevic, Field & Francis LLP

(57) ABSTRACT

An isolated protein comprising a moiety of 90-200 amino acid residues having at least 70% identity to Bri2 BRICHOS, wherein the amino acid residue corresponding to Arg in position 221 in full-length Bri2 wt is not Arg, Lys or His. The protein is useful as a medicament for use in treatment of Alzheimer's Disease.

10 Claims, 13 Drawing Sheets

Specification includes a Sequence Listing.

```
Human     FADSDPANIVHDFNKKLTAYLDLNLDKCYVIPLNTSIVMPPRNLLELLIN
Chimp     FADSDPANIVHDFNKKLTAYLDLNLDKCYVIPLNTSIVMPPRNLLELLIN
Bovine    FADSDPANIVHDFNKKLTAYLDLNLDKCYVIPLNTSIVMPPKNLLELLIN
Pig       FADSDPANIVHDFNKKLTAYLDLNLDKCYVIPLNTSIVMPPRNLLELLIN
Mouse     FADSDPANIVHDFNKKLTAYLDLNLDKCYVIPLNTSIVMPPKNLLELLIN
Rat       FADSDPANIVHDFNKKLTAYLDLNLDKCYVIPLNTSIVMPPRNLLELLIN
Non-id                                             *

Human     IKAGTYLPQSYLIHEHMVITDRIENIDHLGFFIYRLCHDKETYKL
Chimp     IKAGTYLPQSYLIHEHMVITDRIENIDHLGFFIYRLCHDKETYKL
Bovine    IKAGTYLPQSYLIHEHMVITDRIENIDHLGFYIYRLCHDKETYKL
Pig       IKAGTYLPQSYLIHEHMVITDRIENIDHLGFYIYRLCHDKETYKL
Mouse     IKAGTYLPQSYLIHEHMVITDRIENVDNLGFFIYRLCHDKETYKL
Rat       IKAGTYLPQSYLIHEHMVITDRIENVDHLGFFIYRLCHDKETYKL
Non-id                             *       *
```

Fig 1

A
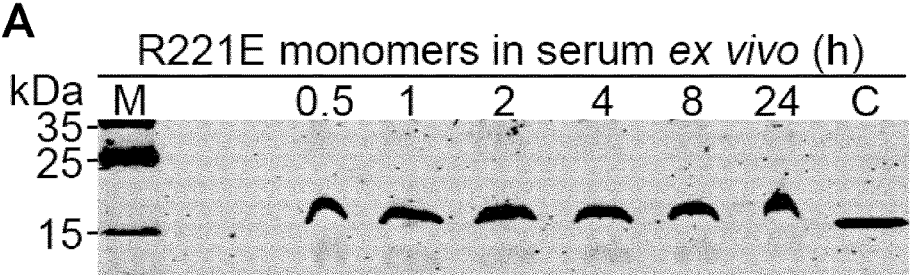
B
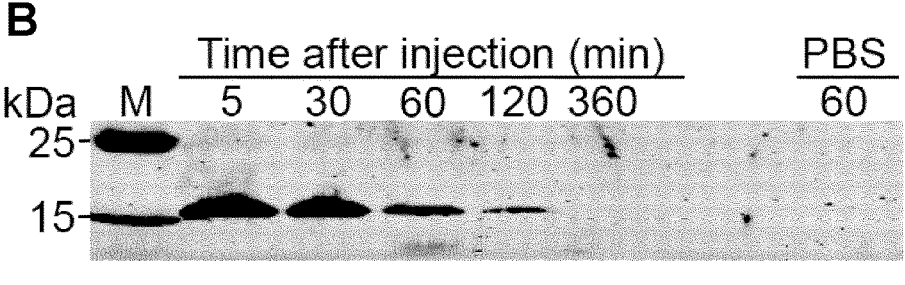
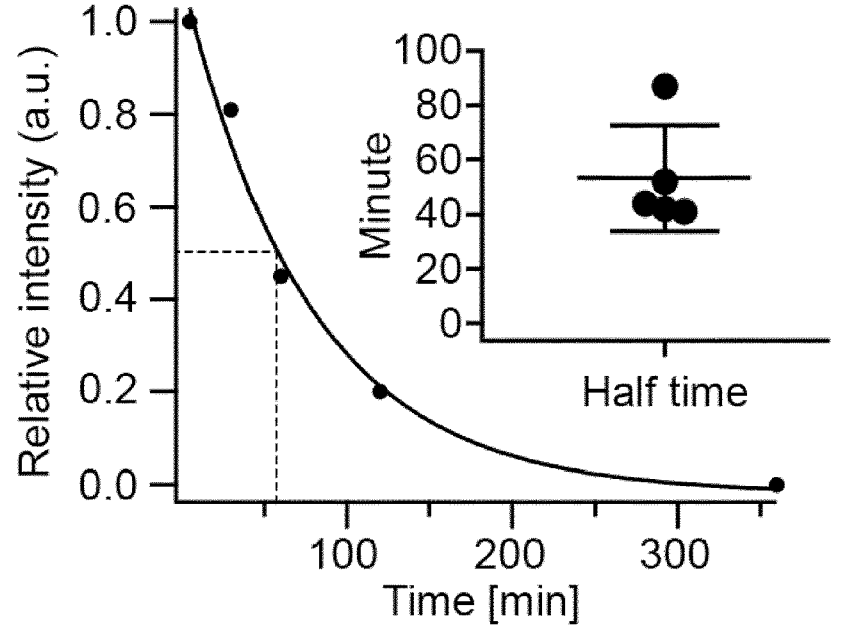
C
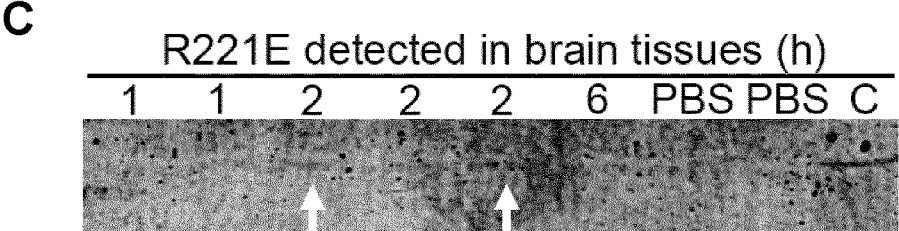
Fig 7

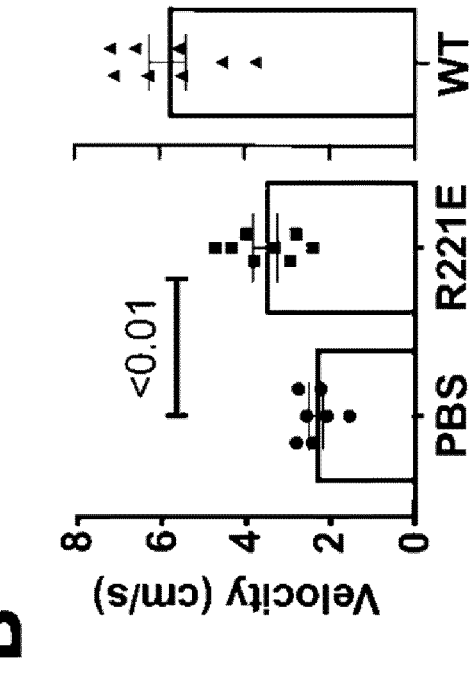
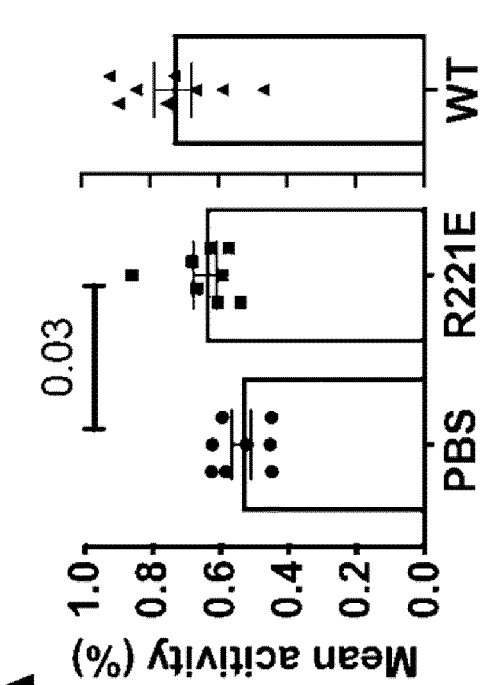
Fig 8

A
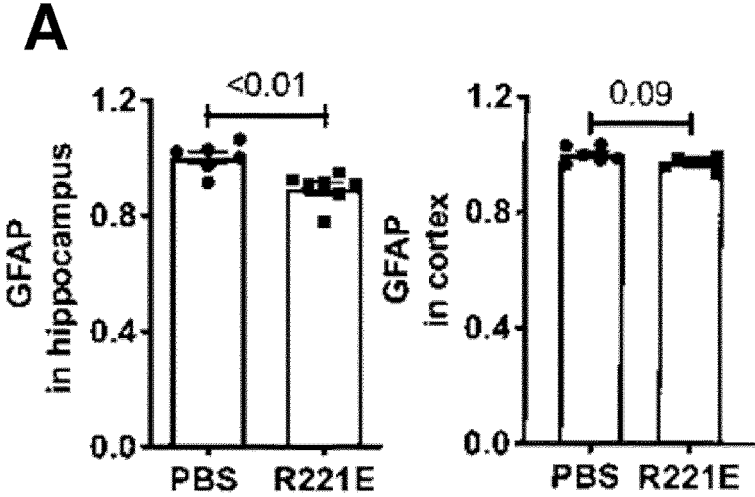
B
C
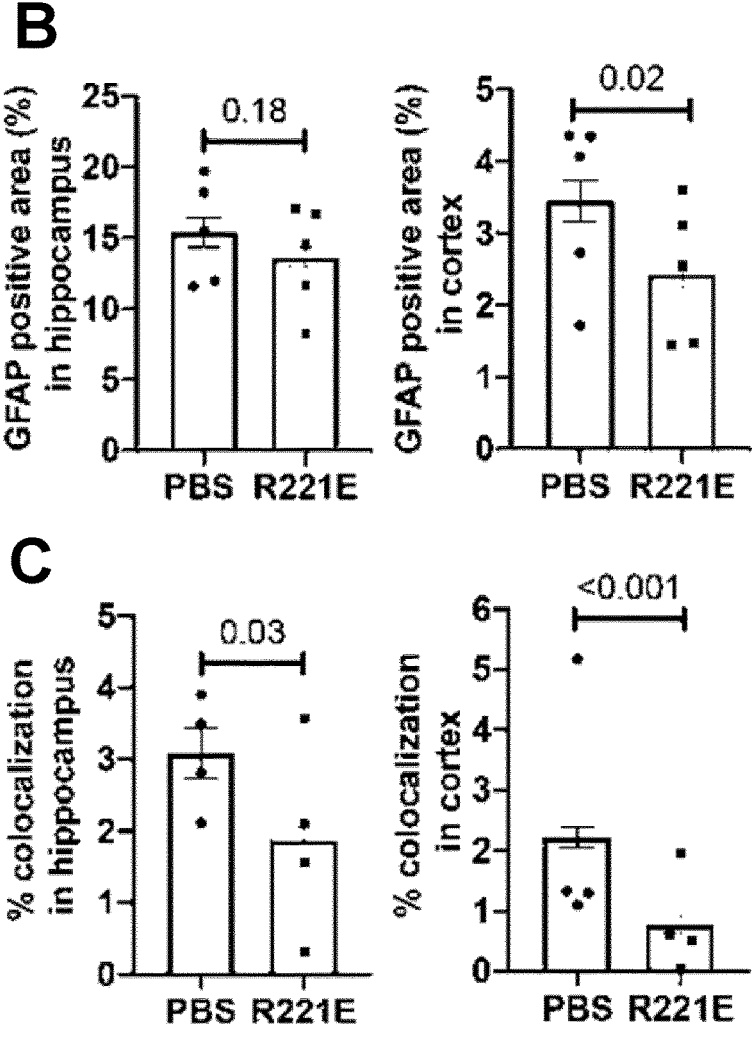
Fig 12

COMPOUND AND METHOD FOR TREATMENT OF ALZHEIMER'S DISEASE

CROSS-REFERENCE TO RELATED APPLICATIONS

This application is a § 371 national phase of International Application No. PCT/EP2021/050168, filed on Jan. 7, 2021, which claims the benefit of European Application No. 20150738.1, filed on Jan. 8, 2020, which applications are incorporated by reference herein.

FIELD OF THE INVENTION

The present invention pertains to the field of medicine. More specifically, this invention relates to medicaments for treatment and medical treatment of Alzheimer's disease in a mammal such as man.

BACKGROUND TO THE INVENTION

Alzheimer's disease is one of the most common causes of dementia in man. It is a chronic and fatal disease associated with neural cell degeneration in the brain of the affected individual, characterized by the presence of amyloid plaques consisting of extracellular deposits of amyloid β-peptide (Aβ-peptide).

Proteolytic processing of the the Aβ precursor protein (AβPP) generates Aβ peptides of different lengths, whereof Aβ42 is the most aggregation prone and toxic. The kinetics of Aβ42 aggregation follows recently defined nucleation-dependent microscopic events. During primary nucleation Aβ42 monomers associate and form a nucleus, from which a fibril can start to elongate. During secondary nucleation, monomers attach to the surface of a fibril, which catalyzes the formation of a new nucleus, leading to exponential fibril growth. This monomer dependent secondary nucleation autocatalytic pathway is the predominant source of toxic Aβ42 species. Key challenges in finding a treatment of AD is to specifically reduce Aβ42 neurotoxicity, rather than focusing on overall aggregation and plaque formation.

One strategy to prevent aggregation has been to utilize molecules that are functionally defined as chaperones. Chaperones play an important role by aiding the correct folding of proteins in the complex intracellular milieu. A number of molecular chaperones, such as heat-shock proteins (Hsp), are known to be important in the folding process and have been extensively studied. Some of these chaperones are apparently able to interact with and have an impact on the amyloid fibril formation of certain polypeptides.

The BRICHOS domain has been found in several human precursor proteins, initially in Bri2, Chondromodulin-1 and prosurfactant protein C (proSP-C). Sanchez-Pulido et al., Trends Biochem Sci 27(7): 329-332,2002 provides a review of BRICHOS domains. The BRICHOS domain has been suggested to prevent amyloid formation of aggregation prone regions (clients) of the respective proprotein during biosynthesis. Recombinant human (rh) BRICHOS domains from proSP-C and Bri2 are efficient inhibitors also of amyloid formation of non-client proteins such as medin, islet amyloid polypeptide, Aβ40 and Aβ42.

WO 2011/162655 discloses that the BRICHOS domain of Bri2 decreases amyloid fibril formation and aggregation of Aβ peptide and ABri/ADan peptides.

Bri2 is produced in the central nervous system (CNS) with expression in neurons of the hippocampus and cortex in humans, and colocalizes with senile plaques in AD patients.

Known sequences of Bri2 include sequences derived from *Erpetoichtys calabaricus* (NCBI accession no. XP_028655526) and *Acipenser ruthenus* (UniProt/TrEMBL accession no. A0A444U9X2). Under physiological conditions, the BRICHOS domain is released by proteolysis from the Bri2 precursor protein. Recombinant human (rh) Bri2 BRICHOS is efficient in inhibiting Aβ42 fibril formation in vitro and in alleviating the related neurotoxicity to hippocampal slice preparations and in *Drosophila* models. Rh proSP-C BRICHOS specifically impedes the secondary nucleation step in Aβ42 fibril formation. Rh Bri2 BRICHOS modulates both elongation and secondary nucleation events, but different assembly states of Bri2 BRICHOS affect Aβ fibril formation in different ways. Bri2 BRICHOS monomers are most potent in preventing Aβ42 induced disruption of neuronal network activity, while dimers most efficiently suppress Aβ42 overall fibril formation and oligomers inhibit non-fibrillar protein aggregation (Chen et al., Nat. Commun., 8: 2081 (2017)). The Bri2 BRICHOS monomers are not long-term stable and form high molecular weight oligomers in a concentration-dependent manner in phosphate buffer or in mouse serum in vitro, which is accompanied by reduced potency against Aβ42 fibril formation. Conversion of Bri2 BRICHOS monomers to high molecular weight oligomers may be relevant for AD, as increased amounts of different Bri2 forms were found in AD brain compared with healthy controls. These observations imply that modulating the distribution of Bri2 BRICHOS assembly states so that the amount of monomers is increased is a concept to combat Aβ42 neurotoxicity, see e.g. WO 2012/138284.

Despite these advances in the art, there is a strong need of improved and alternative therapies for treatment of conditions associated with formation of amyloid protein fibrils in a mammal, such as man.

SUMMARY OF THE INVENTION

It is an object to decrease the tendency of proteins that are prone to fibrillate to aggregate into amyloid fibrils, or even prevent proteins that are prone to fibrillate from aggregating into amyloid fibrils.

It is also an object to decrease formation of amyloid plaques consisting of extracellular deposits in the brain of a mammal of proteins that are prone to fibrillate.

It is also an object to provide a new treatment option for the treatment of Alzheimer's disease.

It is yet another object to provide compounds, combinations of compounds and pharmaceutical compositions comprising such compounds for the treatment of Alzheimer's disease.

It is an object to modulate the distribution of Bri2 BRICHOS assembly states so that the amount of monomers is increased in order to combat Aβ42 neurotoxicity.

The present invention is generally based on the insight that monomers of chaperone proteins which have a high identity to the BRICHOS domains of Bri2 from human are useful for medical treatment Alzheimer's disease. Here, we design a single point mutant of Bri2 BRICHOS that stabilizes the monomeric state. This mutant monomer is potent in preventing Aβ42 neurotoxicity, specifically suppresses secondary nucleation during fibril formation and, importantly, significantly potentiates wild-type (wt) protein against Aβ42 neurotoxicity.

For these and other objects that will be evident from the following description, the present invention provides according to different aspects a new isolated protein; a pharmaceutical composition comprising the protein; use of the protein as a medicament use in treatment of Alzheimer's Disease; and a method of treating Alzheimer's Disease comprising administration of the protein.

BRIEF DESCRIPTION OF THE DRAWINGS

FIG. 1 shows an alignment of some mammalian Bri2-Brichos amino acid sequences (SEQ ID NOS: 7-12).

FIG. 7 illustrates that Bri2 BRICHOS R221E forms stable monomers that pass the blood-brain barrier (BBB).

FIG. 8 illustrates behavioural effects of Bri2 BRICHOS R221E in mice having Alzheimer like pathology.

FIG. 12 illustrates glial fibrillary acidic protein (GFAP) levels and co-localization with Aβ in brain tissues.

LIST OF APPENDED SEQUENCES

Figure 2:
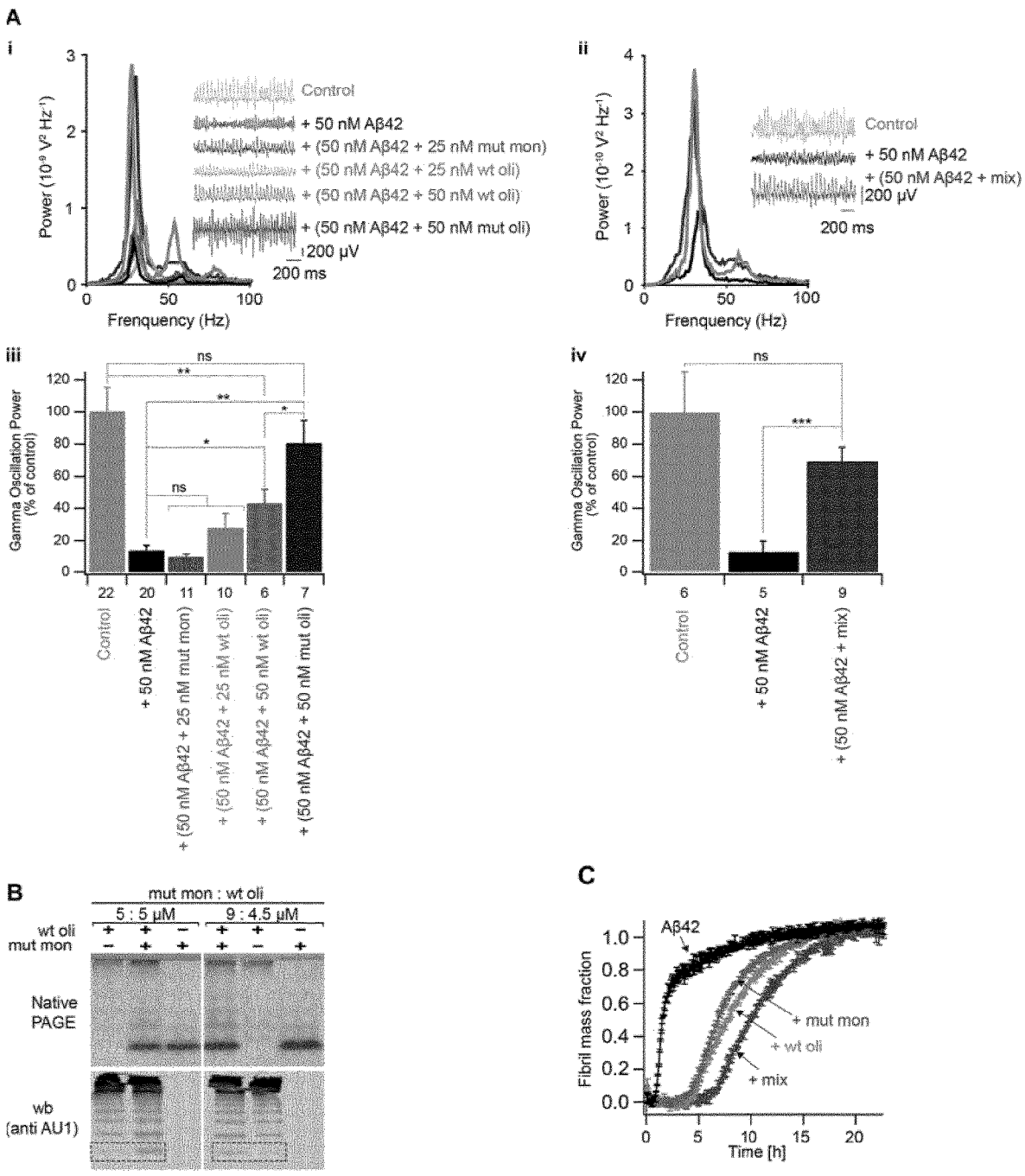
FIG. 2 shows that Bri2 BRICHOS R221E monomers potentiate wt Bri2 BRICHOS oligomers against Aβ42 neurotoxicity by means of (A) γ oscillation data, (B) native PAGE and western blot, and (C) ThT kinetic analysis.

| | |
|---|---|
| SEQ ID NO: 1 | human Bri2 |
| SEQ ID NO: 2 | NT*-Bri2 BRICHOS mutant |
| SEQ ID NO: 3 | Bri2 BRICHOS [Bri2(113-231)] |
| SEQ ID NO: 4 | Bri2 BRICHOS [Bri2(113-231)] mutant |
| SEQ ID NO: 5 | human Bri2(1-89) |
| SEQ ID NO: 6 | human Bri23 [Bri2(244-266)] |
| SEQ ID NO: 7 | human Bri2$_{Brichos}$ [Bri2(137-231)] |
| SEQ ID NO: 8 | chimpanzee Bri2$_{Brichos}$ |
| SEQ ID NO: 9 | bovine Bri2$_{Brichos}$ |
| SEQ ID NO: 10 | pig Bri2$_{Brichos}$ |
| SEQ ID NO: 11 | mouse Bri2$_{Brichos}$ |
| SEQ ID NO: 12 | rat Bri2$_{Brichos}$ |
| SEQ ID NO: 13 | human Bri2$_{Brichos}$ [Bri2(137-231)] mutant |
| SEQ ID NO: 14 | forward PCR primer |
| SEQ ID NO: 15 | reverse PCR primer |
| SEQ ID NO: 16 | NT*-Bri2 BRICHOS mutant [DNA] |

DETAILED DESCRIPTION OF THE INVENTION

Bri2 (SEQ ID NO: 1), also referred to as integral membrane protein 2B (ITM2B), contains an evolutionary conserved Brichos domain spanning residues 137-231 (FIG. 1, SEQ ID NO: 7-12). The Brichos domain of Bri2 may alternatively be considered as spanning residues 113-231 (SEQ ID NO: 3).

The present invention is generally based on the insight that monomers of chaperone proteins which have a high identity to the BRICHOS domains of Bri2 from human are useful for medical treatment of Alzheimer's disease. Here, we design a single point mutant of Bri2 BRICHOS that stabilizes the monomeric state. It is stable during long-term incubation in mouse serum and blood-brain barrier (BBB) permeable. This mutant monomer is potent in preventing Aβ42 neurotoxicity, specifically suppresses secondary nucleation during fibril formation and, importantly, significantly potentiates wild-type (wt) protein against Aβ42 neurotoxicity. Systemic administration of the single point mutant of Bri2 BRICHOS shows an improvement in the memory response and behaviour of AD mice. It also shows reduction in astrocyte mediated neuroinflammation.

It is also demonstrated herein that treatment of aged Aβ precursor protein (APP) knock-in mice, that have established Alzheimer-like pathology, with repeated intravenous injections of rh Bri2 BRICHOS R221E improves open field activity and reduces astrogliosis, microgliosis and Aβ plaque burden to extents that agree quantitatively with the reduction of Aβ42 oligomer generation and neurotoxicity predicted in vitro. These results show that chaperone effects against Aβ42 mediated toxicity in vitro can be translated to a clinically relevant treatment in an Alzheimer mouse model with advanced pathology.

According to a first aspect, there is provided an isolated protein selected from the group consisting of proteins comprising a moiety of 90-200 amino acid residues having at least 70% identity to one of the Brichos domains of Bri2 from human having SEQ ID NO: 7 or SEQ ID NO: 3, wherein the amino acid residue corresponding to position 221 (Arg) in SEQ ID NO: 1 is not Arg, Lys or His. For avoidance of doubt, the Arg residue in position 221 of SEQ ID NO: 1 corresponds to the Arg residue in position 109 of SEQ ID NO: 3, and to the Arg residue in position 85 of SEQ ID NO: 7.

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gin, Asn, Ser, Thr and Tyr are similar. The remaining natural amino acid Gly is not similar to any other amino acid in this context.

Throughout this description, alternative embodiments fulfil, instead of the specified percentage of identity, the corresponding percentage of similarity. Other alternative embodiments fulfil the specified percentage of identity as well as another, higher percentage of similarity, selected from the group of preferred percentages of identity for each sequence. For example, the isolated protein sequence may be 70% similar to another protein sequence; or it may be 70% identical to another sequence; or it may be 70% identical and furthermore 90% similar to another sequence.

For avoidance of doubt, the amino acid sequence having at least the given identity to the Brichos domain of Bri2 from human consists of more than or equal to 70, such as more than or equal to 80, such as more than or equal to 90 amino acid residues. A preferable size range is 70-140 amino acid residues, such as 80-140 amino acid residues, e.g. 90-140 amino acid residues.

It is noted that the Brichos domains of Bri2 from human (SEQ ID NO: 7), chimpanzee (SEQ ID NO: 8), bovine (SEQ ID NO: 9), pig (SEQ ID NO: 10), mouse (SEQ ID NO: 11) and rat (SEQ ID NO: 12) is highly conserved, see alignment in FIG. 1. Without desiring to be bound to any specific theory, it is contemplated that the Brichos domain harbours the desired activity with respect to the $A\beta$ peptide. It is preferred that the isolated protein is selected from the group consisting of proteins comprising an amino acid sequence having at least 80%, preferably at least 90%, such as at least 95%, identity to any one of the Brichos domains of Bri2 from human, including SEQ ID NO: 7 and SEQ ID NO: 3. In a preferred embodiment, the isolated protein contains all amino acid residues that are conserved in the Brichos domains of Bri2 from human (SEQ ID NO: 7), chimpanzee (SEQ ID NO: 8), bovine (SEQ ID NO: 9), pig (SEQ ID NO: 10), mouse (SEQ ID NO: 11) and rat (SEQ ID NO: 12), i.e. all amino acid residues of SEQ ID NO: 7 except for residues 42, 76 and 82 (corresponding to residues 178, 212 and 218 in full-length Bri2, SEQ ID NO: 1). In specific embodiments, the isolated protein is selected from the group consisting of proteins comprising any one of the Brichos domains of Bri2 from human including SEQ ID NO: 7 and SEQ ID NO: 3, i.e. it contains one of these Brichos domains, but wherein the amino acid residue corresponding to position 221 (Arg) in SEQ ID NO: 1 is not Arg, Lys or His.

In one variant, the isolated protein is selected from the group consisting of proteins having at least 70%, such as at least 80%, preferably at least 90%, such as at least 95%, or even 100% identity to Bri2 from human (SEQ ID NO: 1), but wherein the amino acid residue corresponding to position 221 (Arg) in SEQ ID NO: 1 is not Arg, Lys or His. In a specific embodiment, the isolated protein is SEQ ID NO: 1, but wherein the amino acid residue corresponding to position 221 (Arg) in SEQ ID NO: 1 is not Arg, Lys or His.

In specific embodiments, the isolated protein is selected from the group consisting of any one of the Brichos domains of Bri2 from human including SEQ ID NO: 7 and SEQ ID NO: 3, i.e. it contains one of these Brichos domains, but wherein the amino acid residue corresponding to position 221 (Arg) in SEQ ID NO: 1 is not Arg, Lys or His.

In the isolated protein disclosed herein, the amino acid residue corresponding to position 221 in SEQ ID NO: 1 is preferably selected from the group consisting of Glu, Asp, Gln and Asn, more preferably from the group consisting of Glu and Asp.

In the isolated protein disclosed herein, the amino acid residue corresponding to position 221 in SEQ ID NO: 1 is preferably Glu. Alternatively, the amino acid residue corresponding to position 221 in SEQ ID NO: 1 may also be Asp.

In certain isolated proteins disclosed herein, the moiety has the amino acid sequence of SEQ ID NO: 4 or the amino acid sequence of SEQ ID NO: 13. Examples of specific isolated proteins include proteins which have the amino acid sequence of SEQ ID NO: 4 or the amino acid sequence of SEQ ID NO: 13.

A preferred group of isolated proteins disclosed herein is the monomer fraction thereof. One preferred method of providing a monomer fraction is separation by Size Exclusion Chromatography. In a sample of the isolated proteins disclosed herein, it is preferred that at least 25%, such as at least 50%, or at least 75% of the isolated proteins are present as monomers. In a sample of the isolated proteins disclosed herein, it is further preferred that essentially all of the isolated proteins are present as monomers.

The isolated protein is preferably not comprising an amino acid sequence having at least 70% identity to residues 1-89 of Bri2 from human (SEQ ID NO: 5). In certain embodiments, the isolated protein is not comprising an amino acid sequence having at least 50% identity to residues 1-89 of Bri2 from human (SEQ ID NO: 5). This implies that the isolated protein contains a core amino acid sequence which displays a high similarity or identity to the Brichos domain of Bri2 and optionally one or more other amino acid sequences, which other amino acid sequences may not display a high similarity or identity to residues 1-89 of Bri2 from human (SEQ ID NO: 5). For avoidance of doubt, amino acid sequences that are shorter than 10 amino acid residues are not considered relevant in the context of being excluded from the isolated protein. Thus, the isolated protein is not comprising an amino acid sequence that consists of more than or equal to 10 amino acid residues having at least the given identity to residues 1-89 of Bri2 from human (SEQ ID NO: 5).

Furthermore, the isolated protein is preferably not comprising an amino acid sequence having at least 70% identity to residues 244-266 of Bri2 from human, i.e. human Bri23 (SEQ ID NO: 6). In certain embodiments, the isolated protein is not comprising an amino acid sequence having at least 50% identity to residues human Bri23 (SEQ ID NO: 6). As set out above, this implies that the isolated protein contains a core amino acid sequence which displays a high similarity or identity to the Brichos domain of Bri2 and optionally one or more other amino acid sequences, which other amino acid sequences may not display a high similarity or identity to human Bri23 (SEQ ID NO: 6).

For avoidance of doubt, amino acid sequences that are shorter than 10 amino acid residues are not considered relevant in the context of being excluded from the isolated protein. Thus, the isolated protein is not comprising an amino acid sequence that consists of more than or equal to 10 amino acid residues having at least the given identity to human Bri23 (SEQ ID NO: 6).

Proteins comprising a core amino acid sequence having high identity with the Bri2 BRICHOS sequence as set out above may further comprise additional amino acid sequences which do not interfere with the function of the core amino acid sequence, i.e. interaction with $A\beta$ peptides. The additional amino acid sequences may be connected to the N-terminal of the core amino acid sequence, to the C-terminal of the core amino acid sequence, or both. It may also be connected via amino acid side chains, e.g. via a disulphide bond. The additional amino acid sequences may be essentially non-functional or may provide additional functionality to the resulting protein, e.g. solubility, stability or a desired affinity. Both the core amino acid sequence and any additional amino acid sequences may be chemically modified, including post-translational chemical modifications.

In certain embodiments, the isolated protein consists of less than or equal to 500, such as less than or equal to 300, such as less than or equal to 250, such as less than or equal to 200, such as less than or equal to 150 or even 100 amino acid residues. In certain embodiments, the isolated protein consists of more than or equal to 90, such as more than or equal to 100 amino acid residues. A preferable size range is 90-300 amino acid residues, such as 90-200 or 90-140 amino acid residues.

Monomeric Bri2 BRICHOS species most efficiently prevent Aβ42-induced neurotoxicity, and hence their assembly into oligomers result in reduced anti-Aβ42 neurotoxicity. In this study, we designed the R221E Bri2 BRICHOS mutant that forms stable monomers and make rh wt Bri2 BRICHOS oligomers release monomers. Rh Bri2 BRICHOS R221E monomers efficiently alleviate Aβ42 induced neurotoxicity by selectively blocking secondary nucleation, which has previously been shown to constitute a main source of toxic species during Aβ42 aggregation. Moreover, the capacity of rh Bri2 BRICHOS R221E monomers to disassemble wt oligomers results in improved ability to delay Aβ42 fibrillization and, importantly, reduces Aβ42 toxicity to hippocampal slice preparations (FIG. 2).

Means of counteracting proteotoxicity include chaperone-mediated prevention of amyloid formation, disaggregation of pre-existing aggregates, and aggregate sequestration. We rationalized our results in a schematic model to visualize the inhibition efficiencies of the small Bri2 BRICHOS R221E species on specific nucleation events during Aβ42 fibrillization and potential sequestrations of the toxic species (FIG. 6A).

Figure 6:
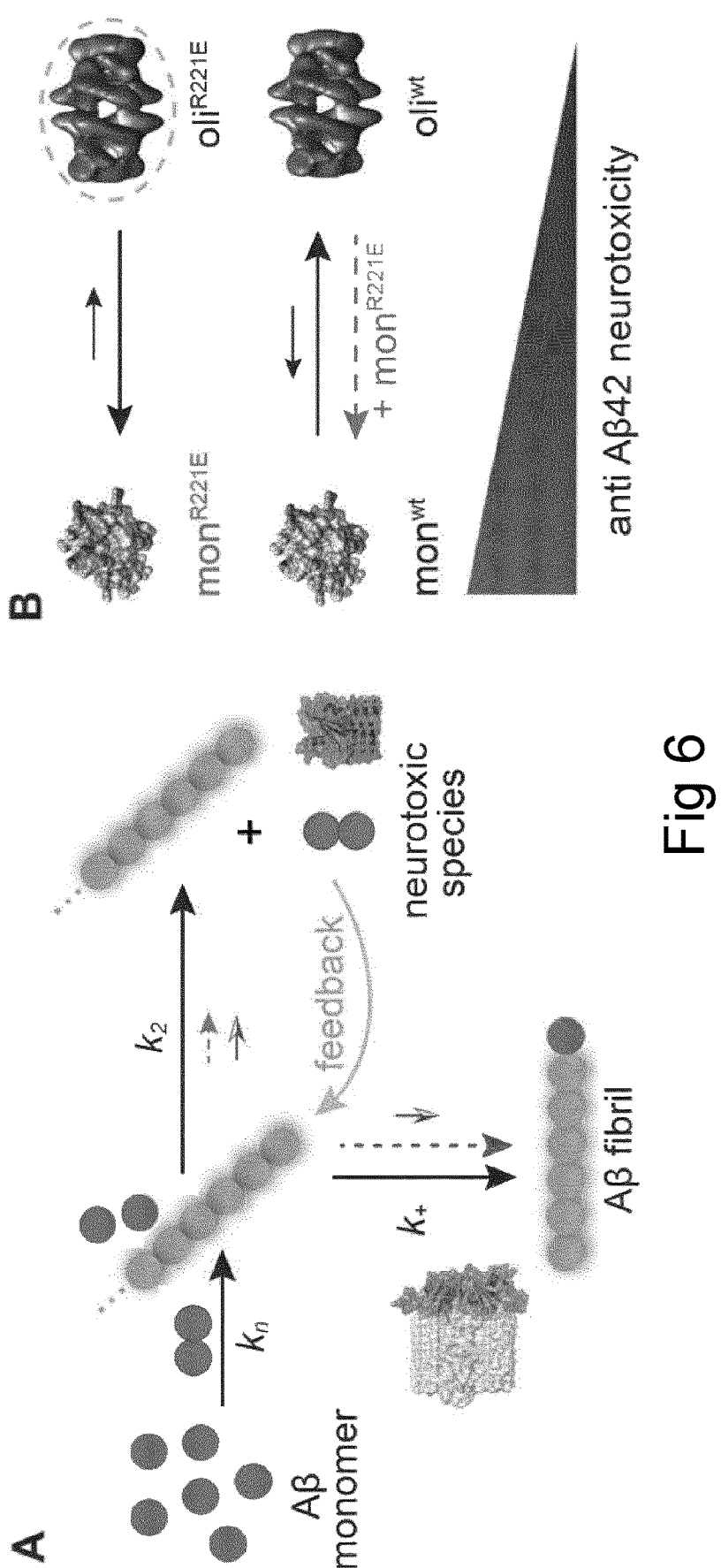
FIG. 6 provides a model for potentiation of chaperone activity against Aβ42 neurotoxicity by shifting the Bri2 BRICHOS assembly state.

FIG. 6. provides a model for potentiation of chaperone activity against Aβ42 neurotoxicity by shifting the Bri2 BRICHOS assembly state:

(A) Aβ42 forms fibrils via primary nucleation, elongation, and secondary nucleation, with rate constants $k_n$, $k_+$, and $k_2$, respectively. While the Bri2 BRICHOS R221E dimer (solid arrows) attenuates both $k_+$ and $k_2$, the monomer (dotted arrows) predominantly reduces $k_2$. Secondary nucleation catalyses the formation of new nucleation units, which acts as a positive feedback loop (curved arrow) for fibril formation, and this mechanism may be linked to enhanced generation of neurotoxic Aβ42 species. Furthermore, the molecular size of the Bri2 BRICHOS monomer fits well to a single layer of β-structured Aβ42 molecules, which might be the structural element of neurotoxic Aβ42 species. On the contrary, the size of the dimer matches well the area of the cross-section of fibril-ends (PDB accession code 5KK3), potentially promoting attenuation of the fibril-end elongation rate. The structural properties together with the specific reduction of $k_2$ may thus make the Bri2 BRICHOS monomer most efficient in prevention of Aβ42-associated neurotoxicity.

(B) Rh Bri2 BRICHOS R221E predominately forms monomers and smaller amounts of oligomers (hypothetical model in dashed circle), while rh wt Bri2 BRICHOS mainly assembles into high molecular weight oligomers (electron microscopy data bank accession code EMD-3918) in equilibrium with monomers. Incubation of rh wt Bri2 BRICHOS oligomers with rh Bri2 BRICHOS R221E monomers destabilizes the oligomers and shifts the kinetic equilibrium toward the monomeric state, leading to an overall increased potency in preventing Aβ42 neurotoxicity (FIG. 2). This model provides thus a basis for understanding how the single point mutation R221E modulates the assembly state of Bri2 BRICHOS and thereby modulates its effects on Aβ42 fibril formation and enhances activities against Aβ42-associated neurotoxicity.

The generation of new nucleation units promoted by secondary nucleation has been suggested to be linked to formation of small neurotoxic A342 species and thus a specific prevention of secondary nucleation events may be beneficial against Aβ42-induced neurotoxicity. Yet, a recent study indicated that also agents that result in an increase in the overall aggregation rate, predominantly caused by an enhanced secondary nucleation rate, can be beneficial to suppress Aβ42 toxicity provided that additional interactions take place. While the detailed mechanism of Aβ42 caused toxicity is still under investigation, efficient toxicity modulators may be especially suited to specifically interact with neurotoxic oligomeric Aβ42 species to shield surfaces that are available for aberrant interactions. These interactions may then hinder the underlying neurotoxic mechanism(s), such as direct binding to receptors or membrane destruction. Interestingly, it has been shown that both intra- and extra-cellular chaperones, including clusterin, Hsp70 and αB-crystallin, can bind to oligomers of several different amyloidogenic peptides, including Aβ, and thereby induce their assembly into larger species that shield reactive surfaces. It remains to be studied whether this mechanism apply to the BRICHOS domain as well, but electron microscopy data suggest that rh Bri2 BRICHOS monomers interact with oligomeric Aβ42 species.

Figure 3:
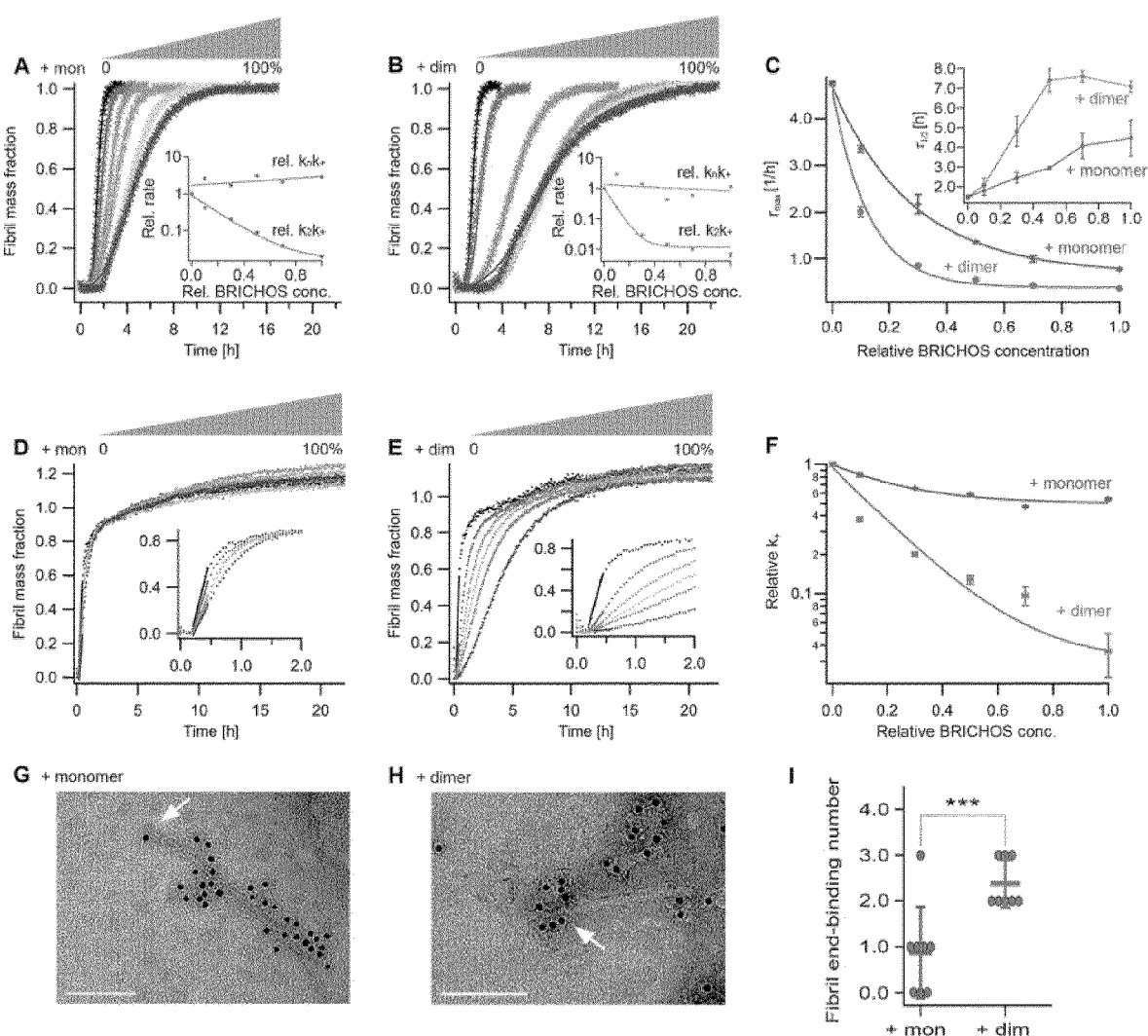
FIG. 3 illustrates the effect of Bri2 BRICHOS R221E monomers and dimers on the microscopic events of Aβ42 fibril formation.

In the current study, we found that the Bri2 BRICHOS R221E monomer predominantly attenuates the secondary nucleation rate, while the dimer substantially affects both the elongation and secondary nucleation rate (FIGS. 3 and 6A). This causes a reduction of the generated number of nucleation units in the presence of Bri2 BRICHOS R221E monomers, but not dimers (FIG. 4A). The molecular size of the Bri2 BRICHOS R221E dimer matches well the surface of the cross-sectional area of recently published Aβ42 fibril structures, providing a possible explanation why the Bri2 BRICHOS dimer, besides the secondary nucleation rate $k_2$, also efficiently attenuates the elongation rate $k_+$. The different specificity of the Bri2 BRICHOS dimer compared to the monomer also support that secondary nucleation and elongation events occur at distinct sites on Aβ42 aggregates. While structural details about the soluble neurotoxic Aβ42 species are still missing, a β-structure state of toxic Aβ42 species/oligomers has been reported. We observed that the molecular size of the Bri2 BRICHOS monomer fits well a single layer of β-structured Aβ42 molecules, which may build up neurotoxic Aβ42 species (FIG. 6A). Hence, the ability to efficiently reduce the generation of new nucleation units together with the well-matched molecular size for interactions with putative neurotoxic Aβ42 species potentially makes the Bri2 BRICHOS monomer most efficient in preventing Aβ42-induced neurotoxicity to hippocampal γ oscillations (FIG. 4B).

For AD aging is the main risk factor, but detailed underlying mechanisms are missing. Chaperone network decline during aging is considered to affect many aging-associated diseases. In aging organisms, the balance between misfolded proteins and functional chaperones is disturbed. Increased amounts of different Bri2 forms were observed in AD brains compared to the healthy controls. Improved chaperone activity could be achieved by increasing the local concentration, but since chaperones are precisely balanced, over-production of certain chaperone may result in disease. Hence, the concept to augment the capacity of certain chaperone networks holds potential for preventing and treating pathologies associated with proteome deterioration. In our current study, augmentation of rh Bri2 BRICHOS activity against Aβ42-induced neurotoxicity is shown to occur as a result of formation of monomeric species from larger oligomers (FIG. 2). The results hence suggest a rational concept to enhance endogenous Bri2 BRICHOS activity against Aβ42-induced neurotoxicity.

According to another aspect, there is provided a nucleic acid comprising a sequence encoding the isolated protein disclosed herein. Exemplary nucleic acids are SEQ ID NO: 16 encoding an NT*-Bri2 BRICHOS mutant and the partial sequences of SEQ ID NO: 16 encoding the Bri2 BRICHOS mutants having SEQ ID NO: 4 and SEQ ID NO: 13.

According to a further aspect, there is provided a pharmaceutical composition comprising a therapeutically effective amount of the isolated protein disclosed herein or the nucleic acid disclosed herein. The pharmaceutical composition also contains a suitable pharmaceutical carrier therefor.

The pharmaceutical composition is useful as a medicament. The pharmaceutical composition is useful in treatment of Alzheimer's disease in a mammal, including man.

According to a related aspect, there is provided a use of the isolated protein for the manufacture of a medicament for the treatment of Alzheimer's disease in a mammal, including man.

A preferred group of isolated proteins which is useful in the pharmaceutical composition is the monomer fraction thereof. One preferred method of providing a monomer fraction is separation by Size Exclusion Chromatography. In the pharmaceutical composition, it is preferred that at least 25%, such as at least 50%, or at least 75% of the isolated proteins are present as monomers. In the pharmaceutical composition, it is further preferred that essentially all of the isolated proteins are present as monomers.

The isolated protein can be incorporated into pharmaceutical compositions. Such compositions typically include the isolated protein and a suitable pharmaceutically acceptable carrier. As used herein, a "suitable pharmaceutical carrier" includes solvents, dispersion media, coatings, isotonic and absorption delaying agents, and the like, that are compatible with pharmaceutical administration. Supplementary active compounds can also be incorporated into the compositions.

A pharmaceutical composition is formulated to be compatible with its intended route of administration. Examples of routes of administration include parenteral (e.g. intravenous, intradermal, subcutaneous, intrathecal, and intracerebral ventricular (e.g. using an Omaya reservoir-shunt with in-line filter that is surgically placed into the cisternal space) administration.

Potentially useful parenteral delivery systems for a composition include slow-dissolving polymer particles, implantable infusion systems, and liposomes. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Treatment of Alzheimer's disease may also be effected by direct delivery of the isolated protein to the central nervous system, preferentially to the brain.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating on particles of the isolated protein (e.g. lecithin), by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents in the composition. Example of such agents include sugars, polyalcohols such as mannitol and sorbitol, and sodium chloride. Prolonged absorption of the injectable compositions can be brought about by including in the composition an agent which delays absorption, for example, aluminum monostearate or gelatin.

Sterile injectable solutions can be prepared by incorporating the isolated protein in the required amount in an appropriate solvent with one or a combination of ingredients enumerated above, as required, followed by filtered sterilization. Generally, dispersions are prepared by incorporating the isolated protein into a sterile vehicle which contains a basic dispersion medium and the required other ingredients from those enumerated above. In the case of sterile powders for the preparation of sterile injectable solutions, the preferred methods of preparation are vacuum drying and freeze-drying, which yield a powder of the isolated protein plus any additional desired ingredient from a previously sterile-filtered solution thereof.

In one embodiment, the isolated protein is prepared with a carrier that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to cells specifically affected by Alzheimer's disease with monoclonal antibodies) can also be used as pharmaceutically acceptable carriers. These can be prepared according to methods known to those skilled in the art.

It is advantageous to formulate oral or parenteral compositions in dosage unit form for ease of administration and uniformity of dosage. Dosage unit form as used herein refers to physically discrete units suited as unitary dosages for the subject to be treated, each unit containing a predetermined quantity of the isolated protein calculated to produce the desired therapeutic effect in association with the required pharmaceutical carrier.

Toxicity and therapeutic effects of the isolated proteins can be determined by standard pharmaceutical procedures in cell cultures or experimental animals, e.g. for determining the $LD_{50}$ (the dose lethal to 50% of the population) and the $ED_{50}$ (the dose therapeutically effective in 50% of the population). Suitable animal models can be used such as those described for amyloidoses in Sturchler-Pierrat et al, Rev Neurosci, 10: 15-24, 1999; Seabrook et al, Neuropharmacol 38: 1-17, 1999; DeArmond et al, Brain Pathology 5: 77-89, 1995; Telling, Neuropathol Appl Neurobiol 26: 209-220, 2000; and Price et al, Science 282: 1079-1083, 1998.

The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to unaffected cells and thereby reduce side effects.

Data obtained from the cell culture assays and animal studies can be used in formulating a range of dosage for use in humans. The dosage of a compound lies preferably within a range of circulating concentrations that include the $ED_{50}$ with little or no toxicity.

The dosage may vary within this range depending upon the dosage form employed and the route of administration utilized. For any compound used in the method, the therapeutically effective dose can be estimated initially from cell culture assays in which, e.g. the rate of fibril formation or the rate of cell death is observed. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of the isolated protein (i.e. an effective dosage) ranges from about 0.1 to 100 mg/kg body weight, more preferably about 1 to 100 mg/kg body weight, and even more preferably about 1 to 50 mg/kg body weight. The compound can be administered over an extended period of time to the subject, e.g., over the subject's lifetime. A dosage of 1 mg/kg to 100 mg/kg is usually appropriate, such as is the case for antibodies designated to act in the brain.

In some cases the compound can be administered for a limited time period. The compound can also be administered chronically. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments.

Recombinant isolated proteins for administration to mice expressing the human APP or to humans can be prepared in several ways. The recombinant proteins can be purified as described herein.

When the isolated protein is to be administered to an animal (e.g. a human) to treat Alzheimer's disease, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration. For example, the instructions can include directions to use the composition to treat an individual having or at risk for Alzheimer's disease.

According to another aspect, there is provided a method of treating Alzheimer's disease, in a mammal, including man, in need thereof comprising administration to said mammal of a therapeutically effective amount of the isolated protein or the pharmaceutical composition.

A preferred group of isolated proteins which is useful in the method of treatment is the monomer fraction thereof. One preferred method of providing a monomer fraction is separation by Size Exclusion Chromatography. In the method of treatment, it is preferred that at least 25%, such as at least 50%, or at least 75% of the isolated proteins are administered as monomers. It is further preferred that essentially all of the isolated proteins are administered as monomers.

In specific embodiments, the treatment may be a preventive treatment. In other specific embodiments, the treatment may be a palliative treatment. In certain specific embodiments, the treatment may be a curative treatment.

The present disclosure provides for both prophylactic and therapeutic methods of treating a subject at risk of (or susceptible to) Alzheimer's disease. As used herein, the term "treatment" is defined as the application or administration of the isolated protein to a patient, or application or administration of the isolated protein to an isolated tissue or cell line from a patient, who has Alzheimer's disease, a symptom of disease or a predisposition toward disease, with the purpose to cure, heal, alleviate, relieve, alter, remedy, ameliorate, improve or affect the disease, the symptoms of disease or the predisposition toward disease.

In one aspect, there is provided a method for preventing a disease or condition (i.e. decreasing the risk of contracting, or decreasing the rate at which symptoms appear that are associated with a disease or condition) associated with fibril formation caused by Aβ peptide by administering to the subject the isolated protein that reduces aggregation of the polypeptide. Subjects at risk for Alzheimer's disease can be identified by, for example, any or a combination of appropriate diagnostic or prognostic assays known in the art. Administration of a prophylactic agent can occur prior to the manifestation of symptoms characteristic of the disease, such that the disease is prevented or, alternatively, delayed in its progression.

The isolated protein can be administered to a patient at therapeutically effective doses to prevent, treat or ameliorate disorders involving fibril formation associated with Alzheimer's disease. A therapeutically effective dose refers to that amount of the compound sufficient to result in amelioration of symptoms of the disorders. Toxicity and therapeutic efficacy of such compounds can be determined by standard pharmaceutical procedures as described above.

It is also contemplated that the protein can be administrated by gene therapy, such as by using expression vectors, plasmids or viruses to transfect cells in the neural system, preferably brain, such that the isolated protein is expressed by these cells in the central neural system. This is useful for the treatment of Alzheimer's disease.

The present invention will now be further illustrated by the following non-limiting examples.

EXAMPLES

Materials and Methods

Bri2 BRICHOS R221E and AU1 Tagged Bri2 BRICHOS Wt Preparation

For generating rh Bri2 BRICHOS R221E (SEQ ID NO: 4), the primers 5'-CACCTGGGTTTCTTTATTTAT-GAACTGTGTCATGACAAGGAAAC-3' (SEQ ID NO: 14) and 5'-GTTTCCTTGTCATGACACAGTTCAT-AAATAAAGAAACCCAGGTG-3' (SEQ ID NO: 15) were synthesized. With the wt NT*-Bri2 BRICHOS (correspond-ing to the solubility tag NT* followed by Bri2 residues 113-231) plasmid as PCR template, Bri2 BRICHOS R221E was obtained with QuikChange II XL Site-Directed Muta-genesis Kit (Agilent, US), and the sequence was confirmed (GATC Bioteq, Germany).

A construct having SEQ ID NO: 16 and coding for a His6-NT*-thrombin cleavage site-Bri2 BRICHOS R221E (SEQ ID NO: 2) was transfected into SHuffle T7 competent *E. coli* cells. The cells were incubated at 30° C. in LB medium containing 15 μg mL-1 kanamycin, until an OD600 nm around 0.9, when the temperature was lowered to 20° C. Isopropyl β-D-1-thiogalactopyranoside (IPTG) was added to 0.5 mM and the cells were incubated overnight. The cells were then harvested by 7,000×g centrifugation at 4° C., after which the cell pellets were resuspended in 20 mM Tris pH 8.0, and sonicated for 5 min on ice (2 s on, 2 s off, 65% power). The lysate was centrifuged (24,000×g) at 4° C. for 30 min and the target protein was purified with a Ni-NTA column. To remove the His6-NT*part, the fusion proteins were cleaved with thrombin (1:1000 enzyme to substrate, w/w) at 4° C. overnight and loaded over a second Ni-NTA column. The resulting Bri2 BRICHOS R221E protein had the amino acid sequence of SEQ ID NO: 4. Different rh Bri2 BRICHOS R221E species (monomers, dimers, oligomers) were separated and analysed by Superdex 200 PG, 200 GL or 75 PG columns (GE Healthcare, UK) using an ÄKTA system (GE Healthcare, UK).

For specific immunodetection, an AU1 tag (DTYRYI) or an mCherry domain was fused to the C-terminal of rh wt Bri2 BRICHOS by PCR amplification. The construct coding for His6-NT*-thrombin cleavage site-Bri2 BRICHOS wt-AU1 or His6-NT*-thrombin cleavage site-Bri2 BRICHOS wt-mCherry were expressed and purified with the same protocol as the one for Bri2 BRICHOS R221E. The rh wt Bri2 BRICHOS-AU1 or rh wt Bri2 BRICHOS-mCherry oligomers were isolated by Superdex 200 PG column (GE Healthcare, UK).

ESI-MS of Bri2 BRICHOS R221E Monomer

Prior to ESI-MS analysis, rh Bri2 BRICHOS R221E (SEQ ID NO: 4) monomers isolated by SEC were buffer exchanged into 200 mM ammonium acetate pH 7.5 using BioSpin microcentrifuge columns (BioRad, US). The final concentration of monomeric subunit was 20 μM. Spectra were recorded on a Waters Synapt G1 mass spectrometer (Waters, Milford, MA) modified for high mass analysis. Samples were introduced into the mass spectrometer using in-house produced gold-coated borosilicate capillaries. Instrument settings were: capillary voltage 1.5 V, sample cone voltage 30 V, extraction cone voltage 4 V, collision trap voltage 50 V, and transfer voltage 10 V. The source pressure was 7 mbar, trap gas was $N_2$ with a flow rate of 8 mL h$^{-1}$. Data analysis was performed using Waters MassLynx 4.1 software.

CD spectroscopy, bis-ANS fluorescence and CS thermal aggregation CD spectra were recorded from 260 to 190 nm at 25° C. in 1 mm path length quartz cuvettes in an Aviv 410 Spectrometer (Lakewood, NJ, USA) with protein concen-tration of 12 μM. The wavelength step was 0.5 nm, aver-aging time 0.3 s, time constant 100 ms, and bandwidth 1 nm. The spectra shown are averages of three consecutive scans. One μM, calculated for the monomeric subunit, of different rh Bri2 BRICHOS R221E species in 20 mM Tris pH 8.0 were incubated with 2 μM bis-ANS (4,4'-Bis(phenylamino)-[1,1'-binaphthalene]-5,5'-disulfonic acid dipotassium salt) for 10 min at 25° C., and fluorescence was recorded with an SLM-Aminco AB-2 spectrofluorimeter and thermostated cuvette holder (Thermo Spectronic, Waltham, MA, USA). The fluorescence emission spectra were recorded from 420 to 600 nm after excitation at 395 nm. CS from porcine heart (Sigma-Aldrich, Germany) was diluted in 40 mM HEPES/KOH pH 7.5 to 600 nM and then equilibrated at 45° C. with and without different concentrations of various rh Bri2 BRICHOS R221E species. The aggregation kinetics were measured in triplicate using a microplate reader (FLUOStar Galaxy from BMG Labtech, Offenberg, Germany) by read-ing the apparent increase in absorbance at 360 nm during incubation at 45° C. under quiescent conditions.

Bri2 BRICHOS R221E Incubation

Rh Bri2 BRICHOS R221E (SEQ ID NO: 4) oligomers, dimers and monomers at 20 μM concentrations (referred to the monomeric subunits) were incubated in ThT assay buffer (20 mM sodium phosphate, pH 8.0 with 0.2 mM EDTA and 0.02% $NaN_3$) at 37° C. Samples were taken out after 0, 1, 4 and 24 h, and analysed for assembly states by SDS-PAGE under reducing and non-reducing conditions. Ten μM rh Bri2 BRICHOS R221E oligomers and monomers were incubated in ThT assay buffer at 37° C. overnight and analyzed by native PAGE. Twenty μM rh Bri2 BRICHOS R221E dimers were also incubated in 20 mM sodium phosphate, pH 8.0 with 0.2 mM EDTA and 0.02% $NaN_3$ at 37° C. overnight and analyzed by native PAGE.

Aβ42 Monomer Preparation and ThT Assay

Recombinant Met-Aβ(1-42), here referred to as Aβ42, was produced in BL21*(DE3) pLysS *E. coli* (B strain) cells and purified by ion exchange. The purified Aβ42 proteins were lyophilized overnight and re-dissolved in 7 M Gdn-HCl and then injected into a Superdex 75 column (GE Healthcare, UK) for monomer isolation in 20 mM sodium phosphate pH 8.0 with 0.2 mM EDTA and 0.02% $NaN_3$. The Aβ42 concentration was calculated from the absorbances at 280 and 300 nm using an extinction coefficient of 1,424 M−1 cm−1 for (A280-A300). Purified Aβ42 monomers were aliquoted in low-binding Eppendorf tubes (Axygene). For analysis of the kinetics of amyloid fibril formation, 80 μL solution containing 3 μM Aβ42 monomer, 10 μM ThT and different concentrations of rh Bri2 BRICHOS R221E (SEQ ID NO: 4) monomer or dimer (all concentrations refer to the monomeric subunit) at molar ratios 0, 10, 30, 50, 70 and 100% relative to Aβ42, were added to each well of half-area 96-well black polystyrene microplates with clear bottom and nonbinding surface (Corning Glass 3881, USA), and incu-bated under quiescent conditions at 37° C. The fluorescence was recorded using a 440 nm excitation filter and a 480 nm emission filter (FLUOStar Galaxy from BMG Labtech, Offenberg, Germany). The aggregation kinetics of Aβ42 at different concentrations in the presence of a constant con-centration (0.9 μM) of rh Bri2 BRICHOS R221E monomers and dimers were measured in the same manner. For Aβ42 seeds preparation, 3 μM Aβ42 monomer was incubated at 37° C. for about 20 h, and the generated fibrils were then sonicated in a water bath for 3 min. For analysis of Aβ42 fibril formation kinetics in the presence of seeds, 80 μL solution containing 3 μM Aβ42, 10 μM ThT, different concentrations of rh Bri2 BRICHOS R221E monomers or dimers at 0, 10, 30, 50, 70 and 100% relative to Aβ42 monomer, and 0.6 μM seeds (calculated from the original A□42 monomer concentration) were added at 4° C. to each well in triplicate of half-area 96-well plates and immediately incubated under quiescent conditions at 37° C. The fluorescence was recorded as described above. The elongation rate constant $k_+$ (see below) in the presence of rh Bri2 BRICHOS R221E monomers or dimers was calculated from the highly seeded experiments. The initial slope of the concave aggregation traces was determined by a linear fit of the first 25-30 min traces. Aggregation traces were normalized and averaged using 3-4 replicates for all the experiments, and data defining one dataset was recorded from the same plate.

Co-Incubation of Rh Bri2 BRICHOS R221E Monomer and Wt Oligomers

Rh Bri2 BRICHOS R221E (SEQ ID NO: 4) monomer (5 μM), rh wt Bri2 BRICHOS oligomer (5 μM) and the mixtures (rh Bri2 BRICHOS R221E monomer and rh wt Bri2 BRICHOS oligomer, 5 μM:5 μM or 9 μM:4.5 μM) were incubated at 37° C. overnight. Then the activities (at equal total rh Bri2 BRICHOS concentration) were tested against Aβ42 fibril formation by ThT assay, and for prevention of Aβ42 neurotoxicity by γ-oscillation measurements in hippocampal slices (see below). The samples were also analysed by native PAGE and western blotting using rabbit anti AU1 antibody (1:1000, Abcam, UK).

Analysis of Aβ42 Aggregation Kinetics

Macroscopic aggregation profiles of Aβ42 in the presence of different concentrations of rh Bri2 BRICHOS R221E (SEQ ID NO: 4) monomers or dimers were fitted to an empirical sigmoidal equation:

$$F=F_0+A/(1+\exp[r_{max}(\tau_{1/2}-t)])$$

Eq. (1)

where $\tau_{1/2}$ is the aggregation half time, $r_{max}$ the maximal growth rate, A the amplitude and $F_0$ the base value. By applying Eq. (1), the $\tau_{1/2}$ and $r_{max}$ were evaluated for aggregation traces with and without rh Bri2 BRICHOS R221E species.

The aggregation traces of the total fibril mass concentration, M(t), is described by the following integrated rate law:

$$\frac{M(t)}{M(\infty)}=1-\left(\frac{B_++C_+}{B_++C_+\cdot\exp(\kappa t)}\cdot\frac{B_-+C_+\cdot\exp(\kappa t)}{B_-+C_+}\right)^{\frac{k_\infty^2}{\kappa \tilde{k}_\infty}}\cdot\exp(-k_\infty t)$$

Eq. (2)

where the additional coefficients are functions of λ and κ:

$$C_+ = \pm\lambda^2/2/\kappa^2$$

$$k_\infty = \sqrt{2\kappa^2/(n_2(n_2+1))+2\lambda^2/n_c}$$

$$\tilde{k}_\infty = \sqrt{k_\infty^2-4C_+C_-\kappa^2}$$

$$B_+ = (k_\infty \pm \tilde{k}_\infty)/2/\kappa$$

which are two combinations of the microscopic rate constants by $$\lambda=\sqrt{2 \cdot k_+k_n\cdot m(0)^{n_c}} \text{ and}$$

$$\kappa=\sqrt{2 \cdot k_+k_2\cdot m(0)^{n_2+1}}\kappa=\sqrt{2 \cdot k_+k_2\cdot m(0)^{n_2+1}}\kappa=\sqrt{2 \cdot k_+k_2\cdot m(0)^{n_2+1}}.$$

The microscopic rate constants $k_n$, $k_+$, and $k_2$ are the primary nucleation, elongation, and secondary nucleation rate constants, respectively, and the parameters $n_c$ and $n_2$ are the reaction orders for primary and secondary nucleation, respectively.

We identified the microscopic events that are inhibited by rh Bri2 BRICHOS R221E by applying Eq. (2) to describe the macroscopic aggregation profiles and comparing the set of microscopic rate constants $k_+k_2$ and $k_nk_+$ required to describe the time evolution of the fibril formation in the absence and presence of chaperone.

First the kinetic traces at different initial Aβ42 monomer concentration with constant rh Bri2 BRICHOS R221E concentration were fitted globally, where $\sqrt{(k_nk_+)}$ and $\sqrt{(k_+k_2)}$ are constrained to the same value across all concentrations. The kinetic data at constant Aβ42 concentration with different rh Bri2 BRICHOS R221E concentrations were then globally analysed by applying this kinetic nucleation model (FIG. 3), where $\sqrt{(k_nk_+)}$ and $\sqrt{(k_+k_2)}$ are free fitting parameters across all concentrations. We also performed a global fit of the kinetic data set at constant Aβ42 concentration and different rh Bri2 BRICHOS R221E concentrations where the fit was constrained such that one fitting parameter was held to a constant value across all rh Bri2 BRICHOS R221E concentrations, while the second parameter was the only free parameter. This procedure results in that only one rate constant, i.e. $k_n$, $k_+$ or $k_2$, is the sole fitting parameter.

To illustrate the generation of nucleation units, we calculated the time evolution of the rate of generation of new fibrils from monomers according to the nucleation rate $r_n(t)$ by $r_n(t)=k_nm(t)^{n_c}+k_2M(t)m(t)^{n_2}$. The number of nucleation units was calculated by integrating the nucleation rate $r_n(t)$ over the reaction.

Immunogold Staining of Aβ42 Fibrils and Transmission Electron Microscopy Analysis Five μM Aβ42 monomer was incubated at 37° C. with 50% rh Bri2 BRICHOS R221E (SEQ ID NO: 4) monomers or dimers for about 15 h, and the fibrils were collected at 4° C. by centrifugation for 1 h at 22,000×g. The fibrils were carefully resuspended in 20 μL 1×TBS, of which 2 μL were applied to formvar coated nickel grids, and incubated for about 5 min. Excess solution was removed with the edge of a Kleenex paper towel. Blocking was performed by incubation in 1% BSA in TBS for 30 min, after which the grids were washed 3×10 min by TBS. The grids were then incubated with goat anti-Bri2 BRICHOS antibody (1:200 dilution) overnight at 4° C., and washed 3×10 min with TBS. Finally the grids were incubated with anti-goat IgG secondary antibody (1:40 dilution) coupled to 10 nm gold particles (BBI Solutions, UK, EM.RAG10) for 2 h at room temperature, and washed 5×10 min with 1×TBS. Excess solution was removed from the grid surface with the edge of a Kleenex paper towel. For staining, 2 μL of 2.5% uranyl acetate was added to each grid (kept about 20 s), and excess solution was removed. The grids were dried for about 20 sec, and analysed by transmission electron microscopy (TEM, Jeol JEM2100F at 200 kV).

Electrophysiological Studies with Bri2 BRICHOS R221E

Experiments were carried out in accordance with the ethical permit granted by Norra Stockholm's Djurförsöksetiska Nämnd (dnr N45/13). C57BL/6 mice of either sex (postnatal days 14-23, supplied from Charles River, Germany) were used in the experiments. The animals were deeply anaesthetized using isofluorane before being sacrificed by decapitation.

The brain was dissected out and placed in ice-cold ACSF (artificial cerebrospinal fluid) modified for dissection. This solution contained 80 mM NaCl, 24 mM NaHCO₃, 25 mM glucose, 1.25 mM NaH₂PO₄, 1 mM ascorbic acid, 3 mM NaPyruvate, 2.5 mM KCl, 4 mM MgCl$_2$, 0.5 mM CaCl$_2$) and 75 mM sucrose. Horizontal sections (350 μm thick) of the ventral hippocampi of both hemispheres were prepared with a Leica VT1200S vibratome (Microsystems, Stockholm, Sweden). Immediately after slicing, sections were transferred to a submerged incubation chamber containing standard ACSF: 124 mM NaCl, 30 mM NaHCO$_3$, 10 mM glucose, 1.25 mM NaH$_2$PO$_4$, 3.5 mM KCl, 1.5 mM MgCl$_2$ and 1.5 mM CaCl$_2$). The chamber was held at 34° C. for at least 20 min after dissection. It was subsequently allowed to cool to ambient room temperature (~22° C.) for a minimum of 40 min. Proteins (Aβ42, rh Bri2 BRICHOS R221E (SEQ ID NO: 4) species and combinations thereof) were added to the incubation solution for 15 min before transferring slices to the interface-style recording chamber for extracellular recordings. While incubating, slices were continuously supplied with carbogen gas (5% CO2, 95% O$_2$) bubbled into the ACSF.

Recordings were carried out in hippocampal area CA3 with borosilicate glass microelectrodes, pulled to a resistance of 3-5 MO. Local field potentials (LFP) were recorded in an interface-type chamber (perfusion rate 4.5 mL per minute) at 32° C. using microelectrodes filled with ACSF placed in stratum pyramidale. LFP γ-oscillations were elicited by applying kainic acid (KA) (100 nM, Tocris) to the bath. The oscillations were allowed to stabilize for 20 min before any recordings were carried out. No Aβ42, rh Bri2 BRICHOS R221E species or combinations thereof were present in the recording chamber either during stabilization of γ-oscillations, or thereafter during electrophysiological recordings. The interface chamber recording solution contained 124 mM NaCl, 30 mM NaHCO$_3$, 10 mM glucose, 1.25 mM NaH$_2$PO$_4$, 3.5 mM KCl, 1.5 mM MgCl$_2$ and 1.5 mM CaCl$_2$).

Interface chamber LFP recordings were performed with a 4-channel amplifier/signal conditioner M102 amplifier (Electronics lab, Faculty of Mathematics and Natural Sciences, University of Cologne, Cologne, Germany). The signals were sampled at 10 kHz, conditioned using a Hum Bug 50 Hz noise eliminator (LFP signals only; Quest Scientific, North Vancouver, BC, Canada), software low-pass filtered at 1 kHz, digitized and stored using a Digidata 1322A and Clampex 9.6 software (Molecular Devices, CA, USA).

Power spectral density plots (from 60 s long LFP recordings) were calculated in averaged Fourier-segments of 8,192 points using Axograph X (Kagi, Berkeley, CA, USA). Oscillation power was calculated by integrating the power spectral density between 20 and 80 Hz. Data is reported as means±standard errors of the means. For statistical analysis the Student's t-test (unpaired) was used. Significance levels are *p<0.05; p<0.01; *p<0.001. All experiments were performed with parallel controls from the same animal/preparation.

NMR Studies with Rh Bri2 BRICHOS R221E Species and Aβ40

Lyophilized 15N-Aβ40 was dissolved in 10 mM NaOH to a concentration of 2 mg mL-1 and sonicated for 2 min in a water-ice bath. The solution was diluted to reach a final Aβ concentration of 75 μM in 16 mM sodium-phosphate buffer, pH 7.4, 0.02% NaN$_3$, 0.2 mM EDTA and 5% D$_2$O. $^1$H-$^{15}$N HSQC spectra were recorded at 8° C. on a 500 MHz Bruker spectrometer, equipped with a cryogenic probe, using 2,048×128 complex points and 32 scans.

Analysis of BBB Passage

Three months old C57BL/6NTac (Taconic, Denmark) male mice were kept under controlled humidity and temperature on a 12-hour light-dark cycle, group-housed (seven per cage) with food and water available ad libitum. All animal experiments were approved by the ethical committees of Södra Stockholm's Djurförsöksetiska Nämnd (dnr S 6-15) and Linköping's etiska nämnd (ID855). Mice received a single i.v. injection of rh Bri2 BRICHOS R221E (SEQ ID NO: 4) monomers, 20 mg/kg, or equal volume of PBS, into the lateral tail vein by using a 0.3 mL syringe with a 30-gauge needle. Before the injections the mice were placed in a single cage under a heat lamp for 5 minutes, in order to dilate the tail veins. The mice were anesthetized with isofluran and intracardially perfused with 40 mL of saline (0.9% NaCl) 1, 2, or 6 h after the injections. Brains were quickly removed and snap-frozen in dry ice and stored at −80° C. until analysis.

Blood samples were collected from the tail vein at 5, 30 60 120 and 360 min after rh Bri2 BRICHOS R221E monomers were injected. The lateral tail vein was punctured using a 27-gauge needle and 50-100 μL of blood was collected at each time point. Blood samples were coagulated, centrifuged at 4° C. for 10 min at 3000 rpm, and serum was collected and stored at −20° C. Before the analysis the samples were diluted 1:5 in 1×PBS.

Mouse tissues were homogenized in 50 mM Tris/HCl (pH 7.4), 150 mM NaCl, 1.0% (v/v) Triton X-100, 0.1% (w/v) SDS and 10 mM EDTA supplemented with protease inhibitors. Brain samples were centrifuged at 4° C. for 30 min at 14000 rpm, then the supernatant was collected and stored at −20° C. The protein concentrations were determined by the Bradford method. Serum and brain samples were prepared in denaturing buffer containing 2% SDS, 0.03 M Tris, 5% 2-mercaptoethanol, 10% glycerol, bromophenol blue, and heated 10 min at 96° C. The sample volume for serum and brain homogenates was normalized so that 100 μg total proteins were loaded per well. Samples were separated on 10% SDS-PAGE gels under reducing conditions and blotted onto nitrocellulose membranes (GE Healthcare). After blotting, the membranes were blocked in 5% milk/PBS for 1 h, followed by incubation with a goat anti-Bri2 BRICHOS antibody (1:300) in 5% milk, 0.1% Tween/PBS overnight at 4° C. The membranes were washed three times with 0.1% Tween/PBS and incubated with a secondary anti-goat antibody (1:10000) for 1 h at RT. After washing, images were acquired using a fluorescent imaging system (Li-Cor, Odyssey CLx).

Serums half-lives were calculated after densitometric analysis of the rh Bri2 BRICHOS R221E monomeric band intensities with ImageJ. The concentrations were expressed as relative intensities and normalized for each curve to the sample intensity at 5 min. The apparent half-life was obtained using GraphPad Prism by a non-linear one phase decay analysis.

Effect of Bri2 BRICHOS R221E in Mice Having Alzheimer Like Pathology

The effect of rh Bri2 BRICHOS R221E in aged APP$^{NLF}$ mice having Alzheimer like pathology was investigated. APP$^{NLF}$ mice express APP at physiological levels and contains Swedish (KM670/671NL) and Beyreuther/Iberian (I716F) mutations (Saito et al., Nature Neuroscience 17(5): 661-663 (2014)). The model is preferable as it overproduces Aβ42 without overexpressing APP.

Study Design

App knock-in female mice harboring the Swedish (KM670/671NL) and Beyreuther/Iberian (I716F) mutations (AppNL-F mice) were aged to 19 months in the animal facility, Huddinge campus, Karolinska Institutet. Mice were caged in groups of three to five individuals and the light-dark condition was 12-h:12-h (lights on 8:00). Mice were randomly divided for PBS or rh Bri2 BRICHOS R221E administration with n=10/group. Mice received PBS or rh Bri2 BRICHOS R221E (SEQ ID NO: 4; 20 mg/kg of body weight) injections intravenously twice every week, for 10 weeks. The mice were anesthetized using 2-4% isoflurane and injected with PBS or rh Bri2 BRICHOS R221E with slow infusion. Two mice from each group died after receiving 14th-16th injections. The study used a battery of behavior and biochemical assays to determine the treatment effects. The experimenters assessing the behavior and biochemical assays were blinded to the intervention group. The behavior experiments were conducted during the light phase (10:00-18:00). The numbers for all biological repeats are given in the respective methods section. Outliers were detected using Rout method (Q=1%) or Grubbs method (Alpha=0.2) using Prism 8 (GraphPad software Inc., CA, USA) and removed. Age-matched wt mice, 23-25 months old, were used for comparisons of some data.

App knock-in female mice harboring the Arctic (E693G) mutation in addition to the Swedish and Beyreuther/Iberian mutations (AppNL-G-F mice) were treated for 12 weeks with intravenous injections of PBS or rh Bri2 BRICHOS R221E (10 mg/kg) every fifth day (total of 17 injections), n=12/group, starting from an age of 3 months.

All the animal handling and experimental procedures were carried out according local ethical guidelines and approved by Södra Stockholm's Djurförsöksetiska Nämnd (dnr S 6-15) and Linköping's animal ethical board (ID 855).

Behavior Studies

Y maze. The Y-maze apparatus made of gray plastic, consisted of three compartments (36×15 cm) that extended from a center platform (15×15×15 cm). Each mouse was placed in one arm facing the center of the maze and then allowed to explore freely for 5 min. The apparatus was cleaned with 70% ethanol to remove any odor cues between each session.

The spontaneous behavior of the mice were manually determined by dividing the number of alterations/(total entries−1).

Elevated plus maze. The apparatus consisted of two opposing open arms (30×5 cm) and two opposing closed arms (30×5 cm, surrounded by 15 cm high, transparent walls) that extended from a center platform (5×5 cm). The maze was elevated 40 cm above the floor in a room with diffuse light. Mice were placed individually in the center of the apparatus facing an open arm and allowed to freely explore the apparatus for 5 min. The apparatus was cleaned with 70% ethanol to remove any odor cues between each session. Time spent in open arms (s) and numbers of entries into an open arm were measured by the video tracking EthoVision® XT software, Noldus (Wageningen, The Netherlands).

Open field and novel object recognition. The open-field arena was a square plastic box (35×35) with 20 cm walls. Each mouse was gently placed in a corner facing the opaque wall and were allowed to freely explore for 5 min for habituation. After a gap of 2 h, mice were placed in same open box with two similar sample objects (Lego) placed diagonally near the corners of the box and allowed to explore them freely. Next day, one of the objects was replaced with a novel object (egg timer) and mice were allowed to explore the two objects for 5 min. The behavior of each mouse was video-monitored and analyzed using EthoVision® XT software, Noldus (Wageningen, The Netherlands). The arena was cleaned with 70% alcohol after each session. The habituation phase was used to analyze the activity of the mice using the activity tracking feature of the Ethovision software. The exploration behavior of mice was analyzed from time the spent for the similar objects during the familiarization phase. The discrimination index was calculated by dividing the time spent exploring the new object over total time spent exploring both objects.

Morris water maze. Mice were trained in a circular pool (1.2 m diameter, 60 cm height) (Ugobasile, Italy) to locate a hidden escape platform (10 cm diameter, 30 cm height). The pool was virtually divided into four equal quadrants identified as northeast, northwest, southeast, and southwest. The tank was filled with tap water at a temperature of 21±2.0 up to 1 cm above the top of the platform and the water was made opaque with milk. The tank was illuminated with 4 lights near the bottom of the tank. The platform was placed in the tank in a fixed position (in the middle of the northwest quadrant). The pool was placed in a large room with diffuse lighting and curtains to hide the experimenter and with a number of extra-maze visual cues. During the acquisition phase, each mouse was trained for 4 trials per day, for four consecutive days with an inter-trial interval of 30 min. Mice were released facing the wall of the pool from one of following starting points: North, East, South, or West and allowed to search the platform for 60 s. During each day the starting position remained constant. If a mouse could not find the platform after 60 s, it was gently guided towards the platform and allowed to stay for 15 s. During the probe trial, reference memory was assessed by removing the platform on the fifth day, 24 h after the last acquisition trial, using same release point for all the mice. A video camera was placed above the center of the pool and connected to a EthoVision® XT video-tracking system, Noldus (Wageningen, The Netherlands). The latency to find the hidden platform was used as a measure of learning. For the Probe trial, the total time spent in the target quadrant was employed as a measure of retention of acquired spatial memory.

Fear conditioning. The mice were trained and tested in conditioning chambers (17×10×10 cm) with a stainless-steel grid floor (Kinder Scientific, USA) surrounded by a sound-attenuating white chest. On the conditioning day, each mouse was individually placed in the conditioning chamber and allowed to explore freely for 2 min, followed by 30s sound (65 dB) and mild foot shock (0.5 mA, 2 s). One more session of sound and footshock were presented with an inter-stimulus interval of 1 min, and the mice were returned to their home cage 30 s after the last footshock. The chambers were cleaned with 70% ethanol to remove any odor cues between each session. One day after the conditioning, mice were placed in the same chamber and allowed to explore freely for 3 min without footshock administration for context based freezing. On 3rd day, mice were placed in a black square chamber placed inside the sound-attenuating white chest and allowed to explore freely for 2 min, followed by 2 min sound during which the freezing response was assessed for cue-based fear conditioning. In each test, freezing time was calculated using Motor Monitor software (Kinder Scientific, USA). Activity corrected freezing was calculated by subtracting the baseline (initial 2 min period of conditioning day for context fear conditioning and initial 2 min period of 3rd day for cued fear conditioning) from total freezing time.

Enzyme-Linked Immunosorbent Assay (ELISA)

Mouse cortex and hippocampus were divided in TRIS soluble (TS) fraction and guanidine-hydrochloride soluble (GS). $A\beta X$-40 and $A\beta X$-42 were quantified using an $A\beta$ ELISA kit (IBL, Japan) according to the manufacturer's instructions.

Thioflavin-S Staining

Five μm thick sections were cut and obtained on Superfrost Plus microscope glass slides from paraffin embedded brain tissue using a microtome and allowed to dry at 37° C. overnight. Sections were deparaffinized by washing in Xylene and in decreasing (99-70%) concentrations of ethanol, followed by staining with 1% filtered Thioflavin-S prepared in distilled water for 1 h in the dark at room temperature. The sections were washed in 70% and 95% of ethanol followed by washing with distilled water. The sections were then incubated with Hoechst nuclear stain, followed by washing with PBS-T thrice and covered with PermaFluor water soluble mounting media. The sections (4 sections/mouse) were then visualized with Nikon Eclipse E800 confocal microscope and imaged (Nikon DS-Qi2 camera) in 2× magnification. Plaques were counted (by a blinded observer) from the total surface of both cortex and hippocampus region.

Tissue Preparation and Immunofluorescence

Mouse tissue sections on glass slides were deparaffinized by washing in Xylene and in decreasing (99-70%) concentrations of ethanol. For antigen retrieval, slides were pressure boiled in citrate buffer solution (0.1 M citric acid and 0.1 M sodium citrate) at 110° C. for 5 min and then washed with tap water followed by PBS-Tween 0.05% for 5 minutes each. Sections were then incubated with TNB blocking buffer (0.1M Tris-HCl pH 7.5, 0.15 M NaCl and 0.5% Blocking Reagent; PerkinElmer, USA) or NGS (normal goat serum, Vector Laboratories, USA) for 30 min at room temperature.

The brain sections were then incubated with anti-Aβ (82E1; IBL, USA) 1:2000 in TNB buffer, anti-GFAP (glial fibrillary acidic protein; Agilent technologies, USA) 1:500 in TNB buffer or anti-Iba1 (Fujifilm Wako, Japan) 1:250 in NGS at 4° C., overnight. Thereafter, sections were incubated with biotinylated anti-mouse or anti-rabbit antibodies (Vector Laboratories; UK) 1:200 in TNB buffer or NGS for 2 hours at room temperature and then incubated with HRP-Conjugated Streptavidin (PerkinElmer; USA) 1:100 in TNB buffer or NGS for 30 min. For signal amplification, samples were incubated for 10 min in tyramide (PerkinElmer; USA) 1:50 in Amplification Reagent.

Finally, samples were incubated for 15 min with slow agitation with Hoechst solution, 1:3000 in PBS-T followed by mounting with PermaFluor Aqueous Mounting Medium (ThermoScientific, USA) and dried overnight. Between each incubation step, samples were washed 3× in PBS-T for 5 min with slow agitation. The sections (4 per mouse) were then visualized with Nikon Eclipse E800 confocal microscope and imaged with Nikon DS-Qi2 camera in 2× and 10× magnifications for further analysis on ImageJ software (National Institutes of Health, MD).

Western Blotting

Cortex and hippocampus tissue (n=4-7/group) were homogenized in RIPA buffer (Thermo Fisher Scientific, USA) with complete protease inhibitor mixture (Sigma-Aldrich, USA). The supernatants obtained were subjected to protein concentration determination using the Bradford protein assay (Bio-Rad, USA). 50 ug protein was then loaded onto 4-20% precast gels (Bio-Rad, USA) and transferred to 0.2 μm nitrocellulose or PVDF membranes (Amersham™ Hybond□, GE healthcare, Germany). Membranes were blocked with 5% skim milk in TBS-T (0.05% Tween-20) and probed with anti-GFAP (Agilent technologies, USA) 1:3000, anti-AIF-1/Iba1 (Novus biologicals, USA) 1:1000, or Anti-Aβ1-16 (6E10; Biolegend, USA) 1:1000 and kept overnight at 4° C. and then incubated with anti-mouse or anti-rabbit Cy3 1:2500 (GE Healthcare, UK), anti-mouse IgG HRP-conjugated 1:5000 (GE Healthcare, UK) or fluorescently labelled anti-rabbit secondary antibody 1:10000 (Li-COR Biosciences, USA). Membranes were washed with TBS-T thrice after each incubation step.

For APP and of CTF α/β fragments, cortex tissue was homogenized in 4× Pipes buffer (Sigma Aldrich, USA) followed by ultra-centrifugation at 70000 rpm for 30 min. The pellet obtained was resuspended in Pipes buffer and measured for protein concentration using Bradford protein assay. 2.5 ug/ul protein was incubated at 37° C. for 30 min followed by chloroform/methanol, 2:1 (v/v), extraction with gentle mixing for 30 min. To the white interface obtained after centrifugation (15000 rpm, 15 min) chloroform/methanol, 2:1 (v/v), was added with gentle mixing for 1 h followed by centrifugation (15000 rpm, 15 min). The pellet was dried using speed vac for 2 min and resuspended in sample buffer (SDS sample buffer containing 9M urea) and kept overnight at room temperature. 40 ug protein was then loaded onto 8-16% precast gels (Bio-Rad, USA), transferred to 0.2 μm nitrocellulose membrane and probed with anti-APP C-terminal antibody (Sigma-Aldrich, USA) 1:5000 for detection of CTFα/β fragments of APP. Anti-β-actin (Sigma-Aldrich, USA) 1:3500 or anti-GAPDH (Sigma-Aldrich, USA) 1:5000 were used as loading controls. Protein bands were visualized using Amersham imager 600 (GE Healthcare) or Odyssey CLx (Li-COR Biosciences, USA) and band intensity was measured with Image J software and normalized with loading control.

Statistical Analysis

All statistical comparisons were performed using Prism 8 (GraphPad software Inc., CA, USA). Normality was checked using Shapiro-Wilk test. Data across different time point points were analyzed by two-way ANOVA with Bonferroni correction for multiple comparisons. All other data was analyzed by multiple t-test or two-tailed Student's t-test. Error propagation was used to account for variation between sections from the same mouse for immunostaining experiments. Variability of the estimates was reported as standard error of the mean (SEM), $p < 0.05$ was considered as statistically significant.

Correlation Analyses

Correlations in rh Bri2 BRICHOS R221E and PBS treated groups. The correlations were calculated pair-wise as Pearson correlation coefficients for all mice in both the PBS treated control group and in mice treated with rh Bri2 BRICHOS R221E. The sample size was 3 to 8 mice. For identification of relevant correlations and trends, we took into account both the correlation coefficients and the two-tailed p-values ($p < 0.05$ or $p < 0.2$) for the comparisons.

Correlations of in vivo result to in vitro and ex vivo results predicted from BRICHOS/Aβ42 ratio in mouse brains. The effect of rh Bri2 BRICHOS R221E treatments for plaque load, plaque number, astrogliosis and microgliosis, where a positive treatment effect corresponds to decreased levels, the relative effect was calculated as the ratio BRICHOS/PBS, while for behavioral studies, where a positive effect upon treatment corresponds to increased levels, the effect was calculated as the ratio PBS/BRICHOS. The error bars of the ratios correspond to the propagated SEM of the individual measures. Comparisons with p-values>0.2 and data from fear conditioning studies (due to no significant treatment effects) were not included in the analysis.

The number of oligomers generated in vitro was estimated from the amount of GS-soluble Aβ42 in cortex brain homogenates of the rh Bri2 BRICHOS R221E treated group, assuming a brain density of 1.04 g/ml. Further the ratio of BRICHOS:Aβ42 in the brain was estimated based on the extent of BBB passage of wildtype rh Bri2 BRICHOS after 2 h (400±150 nM), giving a ratio for BRICHOS:Aβ42 in the AppNL-F mice of 0.14±0.06.

The estimated effect on ex vivo toxicity to hippocampal γ oscillations is (based on previous results, where addition of 100% of either wildtype or rh Bri2 BRICHOS R221E monomer to Aβ42 gave the same γ oscillation values as the non-treated control and an approximate linear response on the rh wildtype Bri2 BRICHOS monomer concentration was found. Hence, we applied this linear relation to calculate the effect on ex vivo toxicity from the estimated in vivo BRICHOS:Aβ42 ratio. The error was estimated from the relative errors from the control, Aβ42 alone and 100% BRICHOS data sets, assuming a linear relation.

Aβ42 levels in human AD patients were estimated from published values for grey and white matter, using a weighted average of 55.4% grey and 44.6% white matter. Applying the same calculations and assumptions, including that BRICHOS has the same BBB permeability in humans as in mice, as described above for the reduction of new nucleation units, the in vivo effect for human AD Aβ42 levels can be estimated, including the published standard deviation values of the Aβ42 levels for the error estimation.

Results

Bri2 BRICHOS R221E Forms Stable Monomers and Unstable Oligomers

The crystal structure of rh proSP-C BRICHOS, the only available high-resolution structure of a BRICHOS domain, shows a homotrimer in which residues from helix 2 point into a pocket of the neighbouring subunit. In a structural model of Bri2 BRICHOS subunit based on the proSP-C BRICHOS structure, Arg221 is surface-exposed in helix 2 and can point into the pocket of a neighbouring subunit. It is believed that the Arg221Glu mutation introduces opposite surface electrostatic potential, destabilizes the oligomer and generates a stable subunit monomer.

Rh Bri2 BRICHOS R221E was produced in fusion with a solubility tag, NT*, that was recently developed based on the N-terminal domain of spider silk proteins. Purified NT*-Bri2 BRICHOS R221E was separated into oligomers, dimers and monomers by size exclusion chromatography (SEC). In contrast to wt protein, the mutant forms to a large extent monomer, suggesting that Arg221 indeed contributes to Bri2 BRICHOS oligomerization. After proteolytic release of the NT*tag, isolated rh Bri2 BRICHOS R221E oligomers are partially linked by intersubunit disulfide bonds, and the dimers are disulfide dependent. Electrospray ionization mass spectrometry (ESI-MS) confirmed the quaternary structure of rh Bri2 BRICHOS R221E monomers isolated by SEC. The mass determined by ESI-MS, 14050.2 Da, is in perfect agreement with the calculated mass, 14050.1 Da, of a monomer in which the two conserved Cys form an intra-molecular disulfide bond. Circular dichroism (CD) spectroscopy showed that the overall secondary structure of monomeric rh Bri2 BRICHOS R221E is similar to wt monomers. In association with formation of oligomers, the negative CD peak around 205-210 nm shifts to the right, indicative of structural stabilisation which is comparable to the pattern observed for rh wt Bri2 BRICHOS. Isolated rh Bri2 BRICHOS R221E monomers, dimers and oligomers bind bis-ANS, evidenced by a marked increase in fluorescence emission intensity compared with free bis-ANS, and a blue shift of the emission maximum from about 533 nm to 480-490 nm. This shows that all rh Bri2 BRICHOS R221E species expose hydrophobic surfaces, which is similar to the situation for the wt species. The abilities of different assembly states of rh Bri2 BRICHOS R221E to prevent non-fibrillar protein aggregation were assessed against thermo-denatured citrate synthase (CS). The dimers and monomers were comparatively inefficient in suppressing CS aggregation, while the oligomers efficiently reduce aggregation of CS, like the case for wt species. Throughout this paper the concentration of different rh Bri2 BRICHOS R221E species is referred to its monomeric subunits.

Isolated rh wt Bri2 BRICHOS monomers form dimers upon increasing concentration as seen by SEC, while rh Bri2 BRICHOS R221E monomers did not show altered migration on SEC at increasing concentration. Likewise, incubation of rh Bri2 BRICHOS R221E monomers in 20 mM NaPi pH 8.0 at 37° C. overnight followed by native PAGE showed that they maintain a monomeric state, which is not the case for the wt protein. Analysis by native PAGE shows that monomers and other low-n species are released from rh Bri2 BRICHOS R221E oligomers after overnight incubation at 37° C., while rh wt Bri2 BRICHOS oligomers do not spontaneously release smaller species during incubation.

Destabilization of Bri2 BRICHOS Oligomers Augments Anti-Aβ42 Neurotoxic Activities To investigate the effects of destabilization of rh Bri2 BRICHOS oligomers on alleviating Aβ42 associated neurotoxicity, we tested the efficacies in preventing Aβ42-induced reduction of γ oscillations in mouse hippocampal slices. Gamma oscillations correlate with learning, memory, cognition and other higher processes and cognitive decline observed in AD patients goes in-hand with a decrease of γ oscillations. Here γ oscillations were induced in horizontal hippocampal slices from wt C57BL/6 mice by superfusing slices with 100 nM kainate (KA) and then allowing them to stabilize for 30 min.

FIG. 2A shows example traces and example power spectra (i and ii) under control conditions (gray), after 15 min incubation with 50 nM Aβ42, 50 nM Aβ42+25 nM pre-incubated rh Bri2 BRICHOS R221E monomer, 50 nM Aβ42+25 nM pre-incubated rh wt Bri2 BRICHOS oligomer, 50 nM Aβ42+50 nM pre-incubated rh wt Bri2 BRICHOS oligomer, 50 nM Aβ42+50 nM pre-incubated rh Bri2 BRICHOS R221E oligomer, and 50 nM Aβ42+a pre-incubated mixture of 25 nM rh wt Bri2 BRICHOS oligomer and 25 nM rh Bri2 BRICHOS R221E monomer. Summary histograms of normalised γ oscillation power (iii and iv) from the experiments are also shown. The numbers under the histograms denote the number of biological replicates, and the data are reported as means±standard errors of the means. Control vs. Aβ42: p<0.0001, ns, no significant difference, *p<0.05, p<0.01, *p<0.001.

Pre-incubation of hippocampal slices with 50 nM Aβ42 for 15 min markedly reduced the power of γ oscillations generated by subsequent KA application (FIG. 2A). Addition of 50 nM rh Bri2 BRICHOS R221E oligomers together with 50 nM Aβ42 resulted in γ oscillations that did not differ from those in non-treated controls, while addition of rh wt Bri2 BRICHOS oligomers with 50 nM Aβ42 resulted in γ oscillations that were significantly lower compared to the non-treated controls and to the γ oscillations obtained after treatment with rh Bri2 BRICHOS R221E oligomers and Aβ42 (FIG. 2A i,iii). These observations suggest that desta-bilization of rh Bri2 BRICHOS oligomers and release of smaller species increases the anti-Aβ42 neuro-toxicity activity. We next hypothesized that rh Bri2 BRICHOS monomers can interfere with rh wt Bri2 BRICHOS oligomer formation and thereby increase the ratio of monomers, which would be expected to increase the potency to counteract Aβ42 neurotoxicity.

To test this hypothesis, we coincubated rh Bri2 BRICHOS R221E monomers and rh wt Bri2 BRICHOS oligomers, after which the distribution of Bri2 BRICHOS assembly states, and effects on Aβ42 fibril formation and neurotoxicity were evaluated. To enable differentiation between wt and R221E rh Bri2 BRICHOS monomers we used a rh wt Bri2 BRICHOS construct containing an AU1 tag, which behaves like the non-tagged wt protein and can be selectively immunodetected using an anti-AU1 antibody. In FIG. 2B, Rh Bri2 BRICHOS R221E monomer and rh wt Bri2 BRICHOS oligomers containing an AU1 tag for immunodetection (5:5 μM and 9:4.5 μM) were co-incubated at 37° C. overnight, and analysed by native PAGE and western blot with an anti AU1 tag antibody. The dashed boxes indicate migration of wt Bri2 BRICHOS monomers. Native PAGE and western blot analysis showed that coincubation of rh wt Bri2 BRICHOS oligomers with rh Bri2 BRICHOS R221E monomer lead to the release of smaller species, especially monomers (FIG. 2B). We used a fusion of Bri2 BRICHOS with mCherry to further study the ability of rh Bri2 BRICHOS R221E to release monomers from wt rh Bri2 BRICHOS oligomers. Coincubation of rh Bri2 BRICHOS R221E monomers and rh Bri2 BRICHOS-mCherry oligomers gives a concentration dependent release of wt monomers that is saturated at about 2:1 molar ratio between mutant and wt oligomers. Addition of rh Bri2 BRICHOS R221E monomer also increases the anti-Aβ42 neurotoxic efficacy of rh wt Bri2 BRICHOS (FIG. 2A). We coincubated 25 nM of rh wt Bri2 BRICHOS oligomers and 25 nM of rh Bri2 BRICHOS R221E monomer overnight at 37° C. and the mixture attenuated Aβ42-induced reduction of γ oscillation power more potently than 50 nM of rh wt Bri2 BRICHOS oligomers pre-incubated in the same way as the mixture (FIG. 2A). Notably, the enhanced efficiency of the mixture cannot be explained by simply adding the efficiencies of the two single species (FIG. 2A), and Aβ42 fibrillization kinetics were more strongly delayed by the incubated mixture of rh Bri2 BRICHOS R221E monomers and rh wt Bri2 BRICHOS oligomers than by the same total concentration of either species alone (FIG. 2C). FIG. 2C shows ThT kinetic analysis of 3 μM Aβ42 alone, in the presence of 3 μM rh wt Bri2 BRICHOS oligomer, 3 μM rh Bri2 BRICHOS R221E monomer, or a pre-incubated mixture of 1.5 μM wt oligomer and 1.5 μM R221E monomer. Hence, these results suggest that shifting the distribution of Bri2 BRICHOS from oligomers to monomers is a way to potentiate the anti-Aβ42 neurotoxic capacity.

Bri2 BRICHOS R221E Monomers Selectively Inhibit Secondary Nucleation of Aβ42 Fibrillization To find out the molecular mechanism underlying the release of small species from the rh wt Bri2 BRICHOS oligomers and how this correlates to the increased capacity against Aβ42 neurotoxicity, we investigated the effects of rh Bri2 BRICHOS R221E monomers and dimers on Aβ42 fibril formation. We used thioflavin ThT fluorescence to monitor kinetics of Aβ42 fibril formation in the absence and presence of different concentrations of rh Bri2 BRICHOS R221E species.

FIG. 3 illustrates the effect of rh Bri2 BRICHOS R221E monomers and dimers on the microscopic events of Aβ42 fibril formation:

(A-B) Individual fits (solid lines) of normalized and averaged aggregation traces (crosses) of 3 μM Aβ42 in the presence of 0, 10, 30, 50, 70 and 100% rh Bri2 BRICHOS R221E monomer (A) and dimer (B) with the combined rate constants $\sqrt{k_n k_+}\sqrt{(k_n k_+)}$ and $\sqrt{(k_+ k_2)}$ as free fitting parameters. The dependencies of the relative combined rate constants obtained from the fits (insets) reveal a strong effect of both rh Bri2 BRICHOS R221E species on secondary nucleation ($k_+ k_2$) but not on primary ($k_n k_+$) pathways.

(C) Values for $r_{max}$ and $\tau_{1/2}$ (inset) extracted from the fitting of Aβ42 aggregation traces in the presence of different concentrations of rh Bri2 BRICHOS R221E species as shown in (A) and (B).

(D-E) Seeded aggregation traces of 3 μM Aβ42 with 0.6 μM preformed Aβ42 fibrils in the presence of 0, 10, 30, 50, 70 and 100% rh Bri2 BRICHOS R221E monomer (D) and dimer (E).

(F) Elongation rates ($k_+$) determined from highly seeded aggregation kinetics in (D) and (E).

(G-H) 5 μM Aβ42 was incubated with and without 50% molar ratio of rh Bri2 BRICHOS R221E monomers (G) or dimers (H) overnight at 37° C. The samples were treated with goat anti Bri2 BRICHOS antibody and a gold-labelled secondary antibody, and characterized by TEM. The scale bars are 100 nm. The arrows indicate the fibril ends.

(I) Number of gold particles located within 30 nm of eight Aβ42 fibril ends after co-fibrillation with rh Bri2 BRICHOS R221E monomers and dimers, respectively. The data are reported as means±standard deviation. ***p<0.001.

The rh Bri2 BRICHOS R221E monomer showed a dose dependent progressive reduction of Aβ42 fibril formation at substoichiometric concentrations, and the aggregation kinetics follows a typical sigmoidal behaviour (FIG. 3A). The fibrillization half-time, $\tau_{1/2}$, increases with increasing rh Bri2 BRICHOS R221E monomer concentration, while the maximum rate of aggregation, $r_{max}$, shows a mono-exponential decline (FIG. 3A,C). The rh Bri2 BRICHOS R221E dimers show similar effects as the monomers, but are more efficient in supressing the overall rate of Aβ42 fibril formation (FIG. 3B,C). The γ-value, $\tau_{1/2} \alpha \, m(0)^\gamma$, where m(0) is the initial Aβ42 monomer concentration, is similar in the absence and presence of both rh Bri2 BRICHOS R221E species, suggesting that in the presence of rh Bri2 BRICHOS R221E, Aβ42 fibrillization still follows mainly monomer-dependent secondary pathways. The final ThT fluorescence intensity, which is an indicator of the mass of mature fibrils, shows a linear increase against Aβ42 concentration, and does not change significantly in the presence of different concentrations of rh Bri2 BRICHOS R221E species.

Aβ42 fibrillization kinetics are described by a set of microscopic rate constants, i.e. for primary ($k_n$) and secondary (monomer-dependent $k_2$ and monomer-independent $k_-$) nucleation as well as elongation ($k_+$). To identify microscopic processes in the fibrillization pathways of Aβ42 that are most affected by different rh Bri2 BRICHOS R221E species, we determined the combined rate constants $\sqrt{(k_n k_+)}$ for primary and $\sqrt{(k_+ k_2)}$ for secondary nucleation events, respectively. We fitted the kinetic model globally at different Aβ42 concentrations and a constant rh Bri2 BRICHOS R221E concentration, where $\sqrt{(k_n k_+)}$ and $\sqrt{(k_+ k_2)}$ are constrained to the same value across all concentrations. We found that the fitting parameter $\sqrt{(k_n k_+)}$ is similar in the presence of either rh Bri2 BRICHOS R221E species as for Aβ42 alone, suggesting that mainly secondary pathways are modulated by rh Bri2 BRICHOS R221E. The results also show that the rh Bri2 BRICHOS R221E dimer is more efficient than the monomer in inhibiting nucleation events related to $k_+ k_2$, i.e. fibril elongation or/and secondary nucleation. To quantitatively elucidate the effects of rh Bri2 BRICHOS R221E on Aβ42 fibrillization, we subsequently fitted the kinetic model individually to a dataset obtained with a constant Aβ42 concentration and different rh Bri2

BRICHOS R221E concentrations (FIG. 3A-C). The analysis revealed that $\sqrt{(k_+k_2)}$ was changed significantly by rh Bri2 BRICHOS R221E while $\sqrt{(k_nk_+)}$ was not (FIG. 3A,B, insets), again suggesting that the secondary nucleation is the main pathway affected. The individual fitting also showed that the dimers are more potent in reducing $\sqrt{(k_+k_2)}$ than the monomer (FIG. 3A,B, insets).

Perturbations of the individual microscopic rate constants $k_+$, $k_n$ and $k_2$ are most relevant since their relative contributions determine the number of newly formed nucleation units, which might be linked to the generation of neurotoxic Aβ42 oligomeric species. To evaluate the effects on individual microscopic processes, we performed global fits of the kinetic data set at constant Aβ42 and different rh Bri2 BRICHOS R221E concentrations, where the fits were constrained such that only one single rate constant, i.e. $k_n$, $k_+$ or $k_2$, is the fitting parameter. The primary nucleation rate $k_n$ or elongation $k_+$ as the sole fitting parameter gave rise to insufficient fits for both rh Bri2 BRICHOS species, which is further confirmed by NMR data showing that neither monomers nor dimers of rh Bri2 BRICHOS R221E interact with Aβ40 monomers. With $k_2$ as the sole free fitting parameter the kinetics were adequately described for rh Bri2 BRICHOS R221E monomers, but not for the dimers. We conclude hence that the rh Bri2 R221E monomer mainly inhibits the secondary nucleation during Aβ42 fibril formation. In contrast, the dimers inhibit both secondary nucleation ($k_2$) and fibril-end elongation ($k_+$).

To further study how the elongation process is affected in the presence of different rh Bri2 BRICHOS species, we determined aggregation kinetics in the presence of a high initial fibril seed concentration, conditions under which the primary and secondary nucleation events are negligible, and only fibril elongation contribute to the increase in the fibril mass. Under these conditions the fibrillization traces typically follow a concave aggregation behaviour (FIG. 3D,E), where the initial slope is directly proportional to the elongation rate $k_+$. These seeding experiments revealed that the rh Bri2 BRICHOS R221E dimer significantly decreases the elongation rate in a dose dependent manner, and already at low concentrations fibril-end elongation is noticeably retarded (FIG. 3E,F). The rh Bri2 R221E monomer, in contrast, showed only slight effects on fibril-end elongation (FIG. 3D,F). This shows that both rh Bri2 BRICHOS R221E species reduce Aβ42 fibrillization via effects on surface catalysed secondary nucleation, while fibril-end elongation is only substantially affected by the rh Bri2 BRICHOS dimers.

The different effects implicate that monomers and dimers associate differently to the fibril ends. To study this, we used anti-Bri2 BRICHOS immunogold-staining and transmission electron microscopy (TEM). We found that both the monomer and dimer bind abundantly and with similar densities to the Aβ42 fibril surfaces (FIG. 3G,H), which support the kinetic analyses and provide a basis for the effects of both rh Bri2 BRICHOS R221E species on secondary nucleation. Further, the numbers of rh Bri2 BRICHOS R221E dimers that bind to Aβ42 fibril ends are significantly higher than for monomers (FIG. 3I), which corroborates the results from kinetic analyses that predominantly the dimer modulates fibril-end elongation.

Bri2 BRICHOS R221E Monomers Efficiently Prevent Aβ42 Neurotoxicity

Relative inhibition of Aβ42 secondary nucleation and elongation may be linked to reduction of formation of toxic low-molecular weight species, as the number of new nucleation units is decreased by inhibiting secondary nucleation but increased by inhibiting elongation. The results shown in FIG. 3F hence could have important implications for the expected amounts of toxic Aβ42 species formed in the presence of rh Bri2 BRICHOS R221E dimers and monomers, respectively. The amounts of new Aβ42 nucleation units were first calculated from the combined rate constants, determined from the global fit of different Aβ42 concentrations in the presence and absence of constant concentration of rh Bri2 BRICHOS R221E, and the Aβ42 fibril elongation rate at 30% molar equivalent of different rh Bri2 BRICHOS R221E species determined from the seeded aggregation experiments (FIG. 3D-F).

Figure 4:
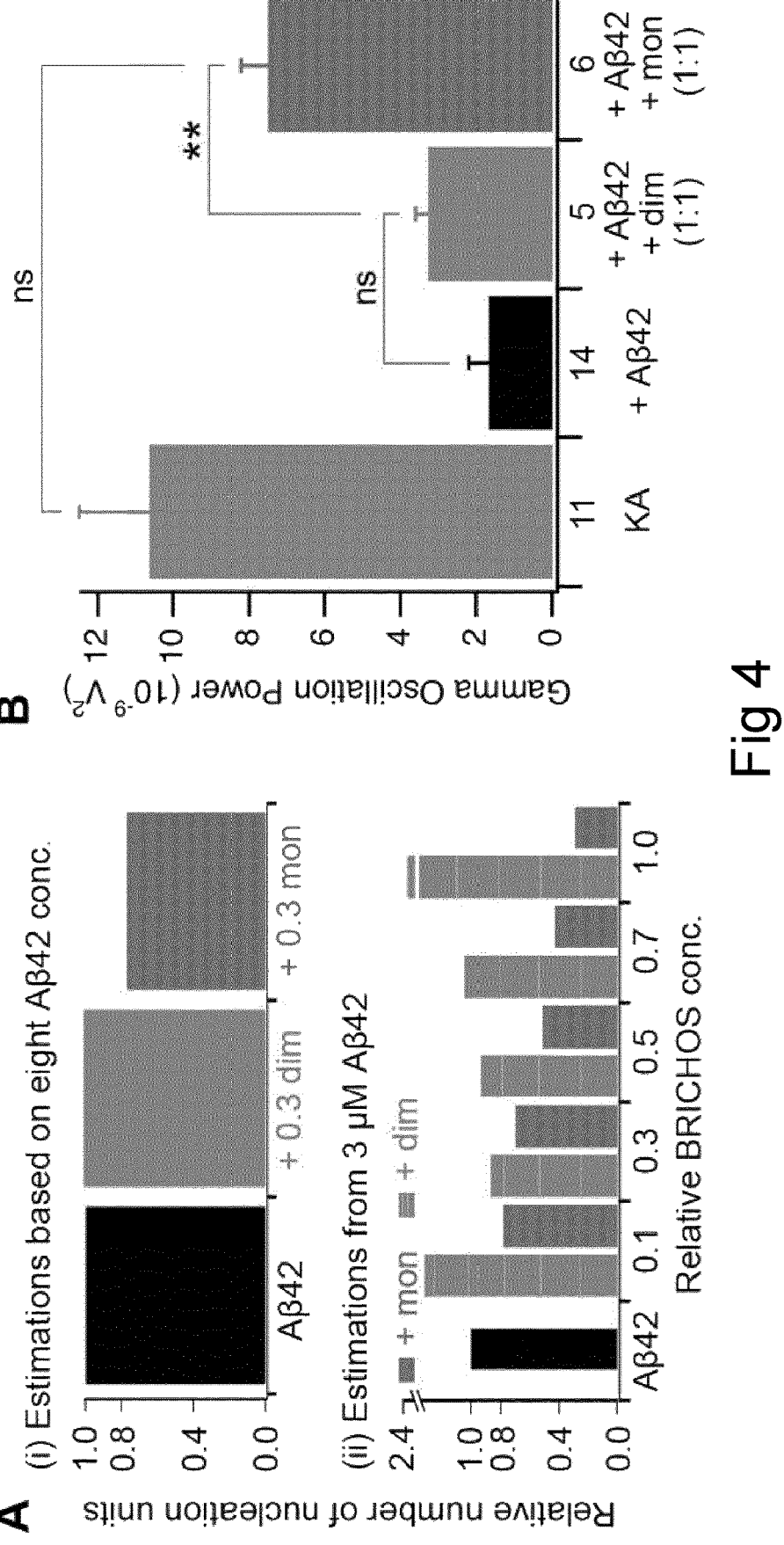
FIG. 4 illustrates the effect of Bri2 BRICHOS R221E monomers and dimers on Aβ42 oligomer formation and neurotoxicity.

FIG. 4 illustrates the effect of rh Bri2 BRICHOS R221E monomers and dimers on Aβ42 oligomer formation and neurotoxicity:

(A) Upper panel: relative numbers of Aβ42 nucleation units formed in the absence or presence of 30% molar ratio rh Bri2 BRICHOS R221E monomers and dimers estimated from the derived global fitting kinetics parameters and the elongation rates ($k_+$) in panel FIG. 3F.

Lower panel: the relative number of Aβ42 nucleation unit formed in the presence of different concentrations of rh Bri2 BRICHOS R221E monomers (right bar) and dimers (left bar) estimated from the individual fitting parameters derived from FIG. 3A,B and the elongation rates ($k_+$) from FIG. 3F.

(B) Summary histograms of mouse hippocampal γ oscillation power under control conditions (KA), after 15 min incubation with 50 nM Aβ42, and after 15 min incubation with 50 nM Aβ42+50 nM rh Bri2 BRICHOS R221E monomers or dimers. The numbers under the histograms denote the number of biological replicates, and the data are reported as means±standard errors of the means. Control vs. Aβ42: p<0.0001; ns, no significant difference; **p<0.01.

The results (FIG. 4A, upper panel) showed that generation of nucleation units is reduced by approx. 25% in the presence of 30% rh Bri2 BRICHOS R221E monomers, while the dimers had no effect. To investigate whether this inhibition effect is also active at higher relative Bri2 BRICHOS concentrations, we next estimated the generation of nucleation units from the combined rate constants obtained from the individual fits (FIG. 3A-B), which are afflicted with a larger uncertainty compared to the values obtained from the global fit, and the elongation rates (FIG. 3F). And indeed, the generation of nucleation units is reduced in a dose dependent manner and up to 70% in the presence of rh Bri2 BRICHOS R221E monomers (FIG. 4A, lower panel). The results hence suggest that rh Bri2 BRICHOS R221E monomers significantly reduce the formation of Aβ42 nucleation units, with an efficiency comparable to that of rh proSP-C BRICHOS, while the dimers do not.

To investigate whether the abilities of rh Bri2 BRICHOS R221E to reduce Aβ42 associated neurotoxicity correlates with the generation of nucleation units, we tested the efficacies of rh Bri2 BRICHOS monomers and dimers in preventing Aβ42-induced reduction of γ oscillations in mouse hippocampal slices. We found that addition of 50 nM rh Bri2 BRICHOS R221E monomer to 50 nM Aβ42 prevented Aβ-induced neurotoxicity and the power of γ oscillations reached the levels of non-treated controls (FIG. 4B). In contrast, addition of 50 nM rh Bri2 BRICHOS R221E dimer to 50 nM Aβ42 did not result in a significant prevention of Aβ42-induced toxicity (FIG. 4B). This indicates that the monomers are efficient against Aβ42-induced toxicity, which supports the kinetics analysis that inhibition of secondary nucleation significantly reduces the toxic Aβ42 oligomer formation.

Figure 5:
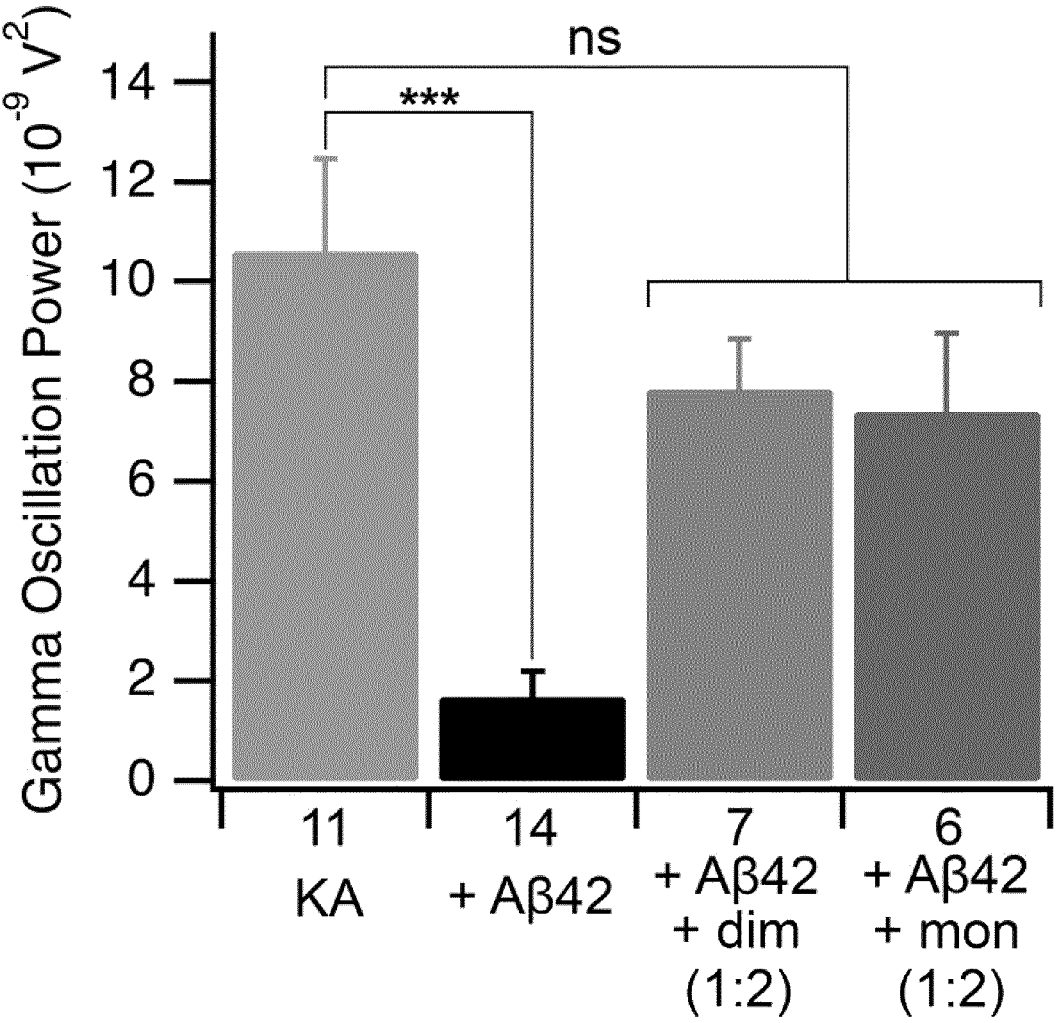
FIG. 5 illustrates the effects on Aβ42 toxicity in mouse hippocampal slices of different Bri2 BRICHOS R221E species.

FIG. 5 illustrates the effects on Aβ42 toxicity in mouse hippocampal slices of different rh Bri2 BRICHOS R221E species. Summary histogram of mouse hippocampal γ oscillation power under control conditions (KA), after 15 min incubation with 50 nM Aβ42, after 15 min incubation with 50 nM Aβ42+100 nM dimers or 100 nM monomers. The numbers under the histograms denote the number of biological replicates, and the data are reported as means±standard errors of the means. *p<0.001; ns, no significant difference. Noteworthily, increasing the concentration of the rh Bri2 BRICHOS dimer from 50 nM to 100 nM resulted in a significant prevention of Aβ42-induced toxicity (FIG. 5**).

These results show that the eventual outcome of inhibitors of Aβ42 fibril formation in terms of effects on neurotoxicity depends both on mechanism of action and molecular ratio relative to Aβ42.

Bri2 BRICHOS R221E Forms Stable Monomers that Penetrate the BBB

FIG. 7 illustrates that rh Bri2 BRICHOS R221E forms stable monomers that pass the BBB:

(A) Western blot after SDS-PAGE under non-reducing conditions of rh Bri2 BRICHOS R221E monomers incubated in mouse serum at 37° C. for different time periods. Lane C contains non-incubated rh Bri2 BRICHOS R221E monomers.

(B) The half-life of rh Bri2 BRICHOS R221E monomers in mouse serum determined by densitometry of western blot bands obtained at different time points after injection. The gel and decay curve show one representative experiment, and the inset shows scatter plot of half-lives determined in five animals. M indicates the proteins ladder.

(C) Western blot after SDS-PAGE under reducing conditions of brain homogenates collected 1, 2, or 6 h after intravenous injection of rh Bri2 BRICHOS R221E monomers or PBS. Lane C shows migration of rh Bri2 BRICHOS R221E monomers. The arrows point out bands in the brain homogenate samples.

Monomers of rh Bri2 BRICHOS R221E were incubated at 37° C. in mouse serum ex vivo, and after 24 h the monomers remained with essentially unchanged intensity (FIG. 7A), while rh wt Bri2 BRICHOS largely converts to oligomers under the same conditions (Chen et al., Nat Commun 8: 2081 (2017)).

Rh BRICHOS R221E monomers at a dose of 20 mg/kg were injected intravenously in C57BL/6NTac mice while control mice received PBS only, and half-life in serum and BBB permeability were evaluated from western blots of serum and brain homogenates, respectively. In vivo, the serum half-life of rh Bri2 BRICHOS R221E monomers is 53±19 min (FIG. 7B), which is longer than the half-life of rh wt Bri2 BRICHOS monomers, dimers or oligomers (around 30-40 min). Rh Bri2 BRICHOS R221E was detected in brain homogenates by western blotting two hours after injection (FIG. 7C), which indicates that rh Bri2 BRICHOS R221E permeates the BBB, like the wt protein.

Effect of Bri2 BRICHOS R221E in Mice Having Alzheimer Like Pathology

The effect of rh Bri2 BRICHOS R221E in aged APP$^{NLF}$ mice having Alzheimer like pathology was investigated.

Figure 9:
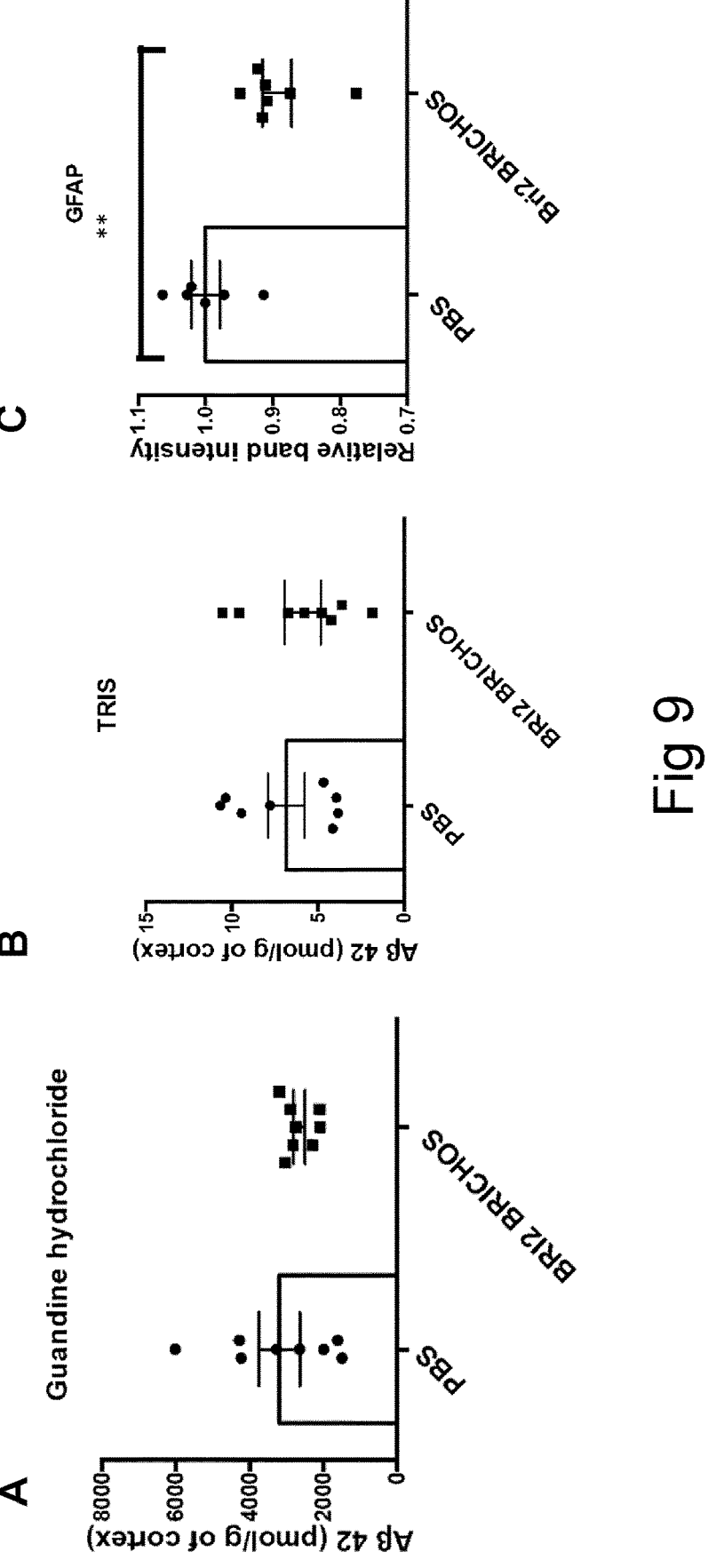
FIG. 9 shows biochemical effects of Bri2 BRICHOS R221E in mice having Alzheimer like pathology.

FIG. 9 illustrates that rh Bri2 BRICHOS R221E administered mice shows a trend towards reduced Aβ42 levels in guanidine hydrochloride (A) soluble fraction of the cortex region, whereas no effect was seen in the Aβ42 levels in the TRIS soluble fraction (B). Rh Bri2 BRICHOS R221E administered mice also showed reduced expression of GFAP (C), an astroglial cell marker implicated in inflammation, suggesting that rh Bri2 BRICHOS R221E parenteral treatment in aged AD mice lowers neuroinflammation.

Thus, systemic administration of rh Bri2 BRICHOS R221E shows reduction in astrocyte mediated neuroinflammation of AD mice.

Physical Activity and Open Field Exploration Improve in Rh Bri2 BRICHOS R221E Administered APP$^{NL-F}$ Mice APP$^{NL-F}$ mice were given a total of 20 injections of rh Bri2 BRICHOS R221E monomer during a 10-week period, which resulted in no macroscopic signs of unwanted side-effects or weight loss compared to PBS injected controls. Rh Bri2 BRICHOS R221E improved the physical activity of mice compared to PBS injected control mice, and their physical activity levels approached the values for age-matched wt mice (FIG. 8A-B).

FIG. 8 illustrates that rh Bri2 BRICHOS R221E improves the physical activity and exploration with no change in anxiety levels in AppNL-F mice. Histograms represent mean activity (FIG. 8A) and velocity (FIG. 8B). Data are shown as mean±SEM for PBS and rh Bri2 BRICHOS R221E treated AppNL-F mice and for age-matched wt controls. Unpaired parametric two-tailed t-test was used to calculate the p-values for all analyses. A 4.99 value in PBS group was removed as an outlier for panel (B).

Aversive Learning and Memory in Rh Bri2 BRICHOS R221E Treated App Knock-In Mice

Fear conditioning (FC) test was performed to evaluate aversive learning and memory response in APP$^{NL-F}$ mice with and without rh Bri2 BRICHOS R221E administration. In the treated App$^{NL-F}$ cohorts, we observed tendencies towards increased freezing behavior in PBS controls compared to rh Bri2 BRICHOS R221E mice for both context and cued FC.

Figure 10:
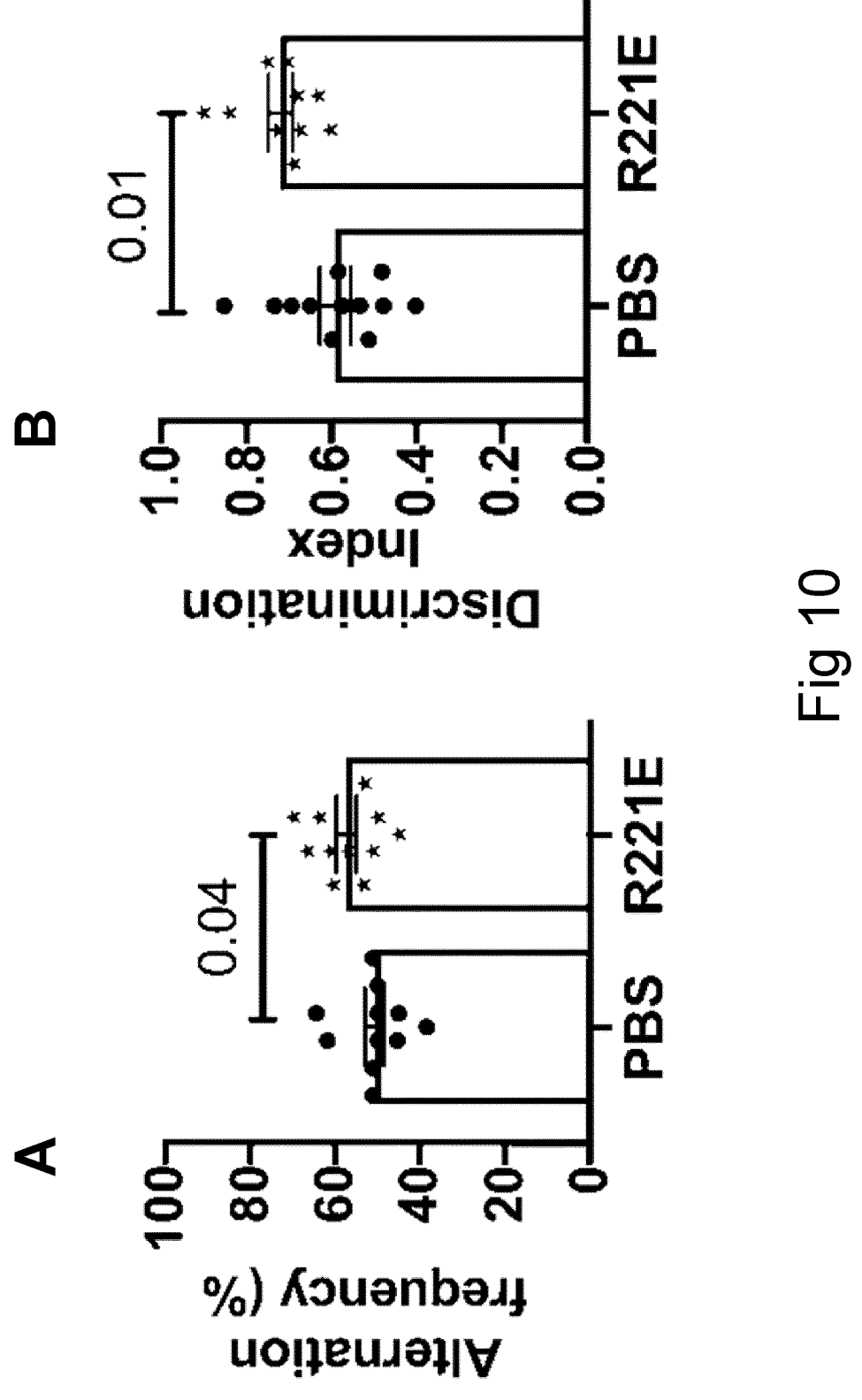
FIG. 10 illustrates learning and memory function in rh Bri2 BRICHOS R221E administered App$^{NL-G-F}$ mice.

App$^{NL-G-F}$ knock-in mice, which carry the Arctic mutation in addition to the Swedish and the Iberian mutations, show a stronger and earlier AD-like pathology, including behavior deficits, compared to App$^{NL-F}$ knock-in mice. We administered rh Bri2 BRICHOS R221E to App$^{NL-G-F}$ knock-in mice from 3 months of age (when Aβ pathology starts to develop) every fifth day for 12 weeks, totally 17 injections, at a dose of 10 mg/kg and thereafter tested them in the Y-maze and evaluated object recognition memory in novel object recognition (NOR). This showed significant (p<0.05) improvements in alternation frequency in the Y-maze (FIG. 10A) and improved novel object discrimination (FIG. 10B) upon rh Bri2 BRICHOS R221E treatment. Data in FIG. 10 are represented as mean±SEM. Two-way ANOVA and unpaired parametric two-tailed t-test were used to calculate the p-values.

Attenuation of Aβ Plaque Burden in App$^{NL-F}$ Mice with Rh Bri2 BRICHOS R221E Treatment Tris or guanidine hydrochloride-soluble Aβ40 and Aβ42 levels in hippocampus and cortex were analyzed by ELISA, which revealed no change in Aβ40 or Aβ42 levels in either brain region between PBS and rh Bri2 BRICHOS R221E treated App$^{NL-F}$ mice. In contrast, staining of brain tissue with Thioflavin S dye for amyloid or immunostaining using Aβ antibody revealed that rh Bri2 BRICHOS R221E treated mice have a lower Thioflavin S positive plaque count in cortex (FIG. 11A) and show a lower total Aβ positive plaque load in cortex (FIG. 11B) compared to PBS controls. Data are represented as mean±SEM. Unpaired parametric two-tailed t-test was used to calculate the p-values.

Reduced Astrogliosis in APP$^{NL-F}$ Mice after Rh Bri2 BRICHOS R221E Treatment

Astrogliosis in cortex and hippocampus was evaluated by glial fibrillary acidic protein (GFAP) levels and by immunostaining of sections of rh Bri2 BRICHOS R221E and PBS administered App$^{NL-F}$ mice. After normalizing with β-actin, the levels of GFAP were significantly (p<0.01) reduced in hippocampal brain homogenates of rh Bri2 BRICHOS R221E treated mice compared to PBS controls and there was a trend towards lower GFAP levels in the cortex in rh Bri2 BRICHOS R221E treated mice (FIG. 12A). Moreover, GFAP immunostaining of brain slices showed that the GFAP positive astrocytes were markedly reduced (p=0.02) in rh Bri2 BRICHOS R221E administered mice in the cortex compared to PBS controls (FIG. 12B). Areas with GFAP positive astrocytes often appeared as circle shaped clusters, indicating that they may surround the plaques. To address this, we double stained brain tissues for GFAP and Aβ and the results show abundant localization of GFAP positive cells around Aβ plaques (FIG. 12C). The extent of GFAP and Aβ colocalization was significantly (p=0.03 or p<0.001) reduced in rh Bri2 BRICHOS R221E treated mice in hippocampus and cortex compared to PBS controls (FIG. 12C). Data are shown for PBS and rh Bri2 BRICHOS R221E treated App$^{NL-F}$ mice as mean±SEM. Unpaired parametric two-tailed t-test was used to calculate p-value for all analyses.

Attenuated Microgliosis in App$^{NL-F}$ Mice with Rh Bri2 BRICHOS R221E Treatment Brain tissue homogenates from cortex and hippocampus were analyzed to evaluate Iba1 levels in rh Bri2 BRICHOS R221E and PBS administered App$^{NL-F}$ mice. The level of Iba1 in cortex of rh Bri2 BRICHOS R221E treated mice was reduced (p=0.05) compared to PBS controls, but there was no detectable difference in the hippocampus region. Iba1 immunostaining of brain slices showed reduced staining in both brain regions indicating fewer Iba1 positive microglial cells in rh Bri2 BRICHOS R221E treated mice compared to PBS controls, with significant (p=0.01) reduction in the cortex region (FIG. 13).

Correlations Between Plaques and Markers for Astrocyte and Microglia Activation in App$^{NL-F}$ Mice with and without Rh Bri2 BRICHOS R221E Treatment Preclinical studies have reported that soluble Aβ oligomers can activate microglia and promote secretion of cytokines. Positron emission tomography imaging in AD subjects of microglia markers and Pittsburgh compound B (PIB), a marker for Aβ deposition, have shown that these markers colocalize in the cortex and also revealed an inverse correlation between cognitive status and microglial activation. Moreover, microglial activation and astrogliosis are potentially early phenomena in AD, but individual levels of PIB positive amyloid deposition and microglial activation are not correlated. This prompted us to clarify potential relationships between plaques and astrocyte and microglia activation from our data. We therefore pair-wise correlated plaque load (Aβ immunostaining), amyloid plaque count (Thioflavin S staining), astrogliosis (GFAP immunostaining), microgliosis (Iba1 immunostaining), and colocalization (Aβ and GFAP immunostaining) in cortex and hippocampus for mice in the PBS treated control group and in the rh Bri2 BRICHOS R221E treated group, respectively.

Figure 13:
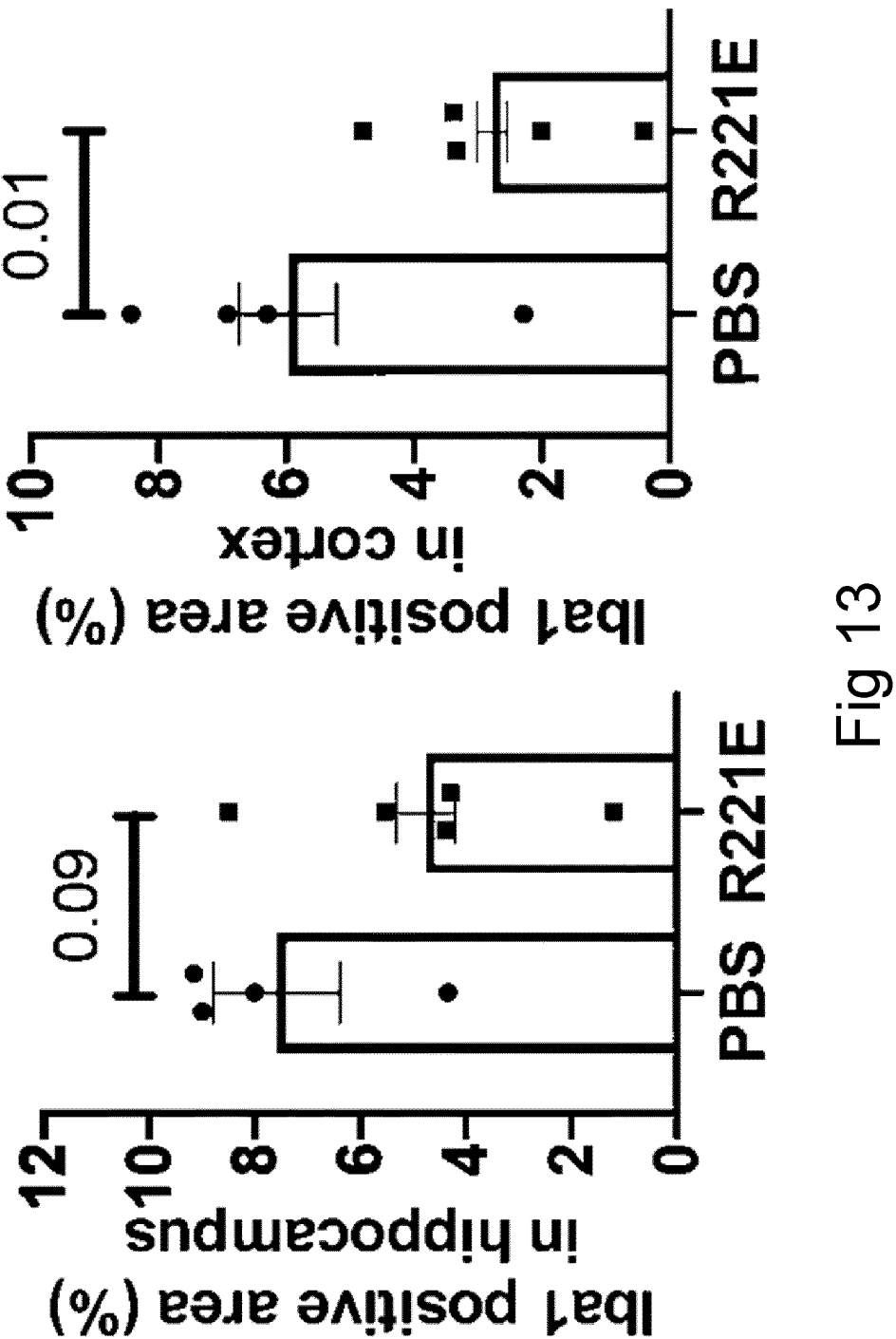
FIG. 13 shows Iba1 levels in brain tissues.

In both PBS and rh Bri2 BRICHOS R221E treated mice, GFAP and Iba1 staining correlate positively in cortex and hippocampus (based on data presented in FIG. 12B and FIG. 13). This is expected since both these markers report on insults to the central nervous system and supports that relevant correlations can be found in our study in spite of the relatively few mice used. This observation also shows that rh Bri2 BRICHOS R221E treatment does not generally suppress correlations compared to PBS controls (see further below). In PBS treated mice, the area of Aβ positive plaques (plaque load) tends to correlate positively with GFAP and Iba1 staining, as well as with Aβ and GFAP colocalization, in particular in cortex (based on data presented in FIG. 11B, FIGS. 12B-C and FIG. 13). Surprisingly, the number of Thioflavin S positive plaques (plaque count) generally correlate negatively with GFAP and Iba1 staining, as well as with Aβ and GFAP colocalization in PBS treated mice (based on data presented in FIG. 11A, FIGS. 12B-C and FIG. 13). Moreover, Aβ plaque load and Thioflavin S plaque counts tend to be inversely correlated with each other in the PBS treated mice (based on data presented in FIG. 11A-B).

Figure 11:
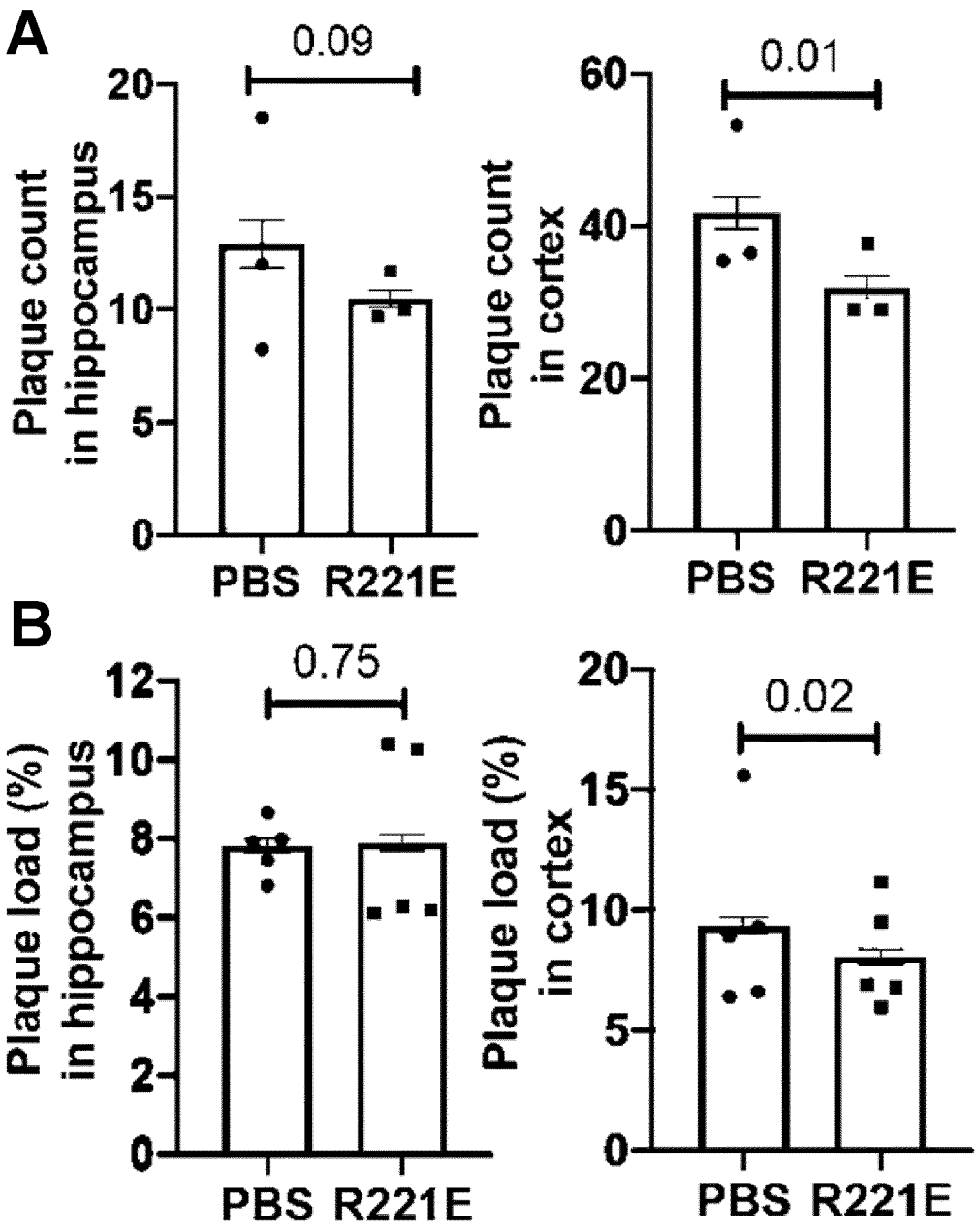
FIG. 11 shows Aβ plaque counts and plaque load with rh Bri2 BRICHOS R221E treatment in App$^{NL-F}$ mice.

In contrast to the situation in PBS treated control App$^{NL-F}$ mice, rh Bri2 BRICHOS R221E treated mice show no correlation between Aβ plaque load and Thioflavin S plaque counts (based on data presented in FIG. 11A-B). Moreover, the trend of negative correlation between Thioflavin S plaque count and GFAP and Iba1 staining seen in PBS mice is not seen in rh Bri2 BRICHOS R221E treated mice (based on data presented in FIG. 11A and FIG. 12B; FIG. 11A and FIG. 13) and the trend of positive correlation between Aβ plaque load and GFAP and Iba1 staining in PBS mice is not visible in rh Bri2 BRICHOS R221E treated mice (based on data presented in FIG. 11B and FIG. 12B; FIG. 11B and FIG. 13).

Effects of Rh Bri2 BRICHOS R221E Treatment in APP$^{NL-F}$ Mice Agree with Reductions of Generation of New Aβ42 Nucleation Units In Vitro and Aβ42 Induced Neurotoxicity Ex Vivo Estimated from Brain BRICHOS/Aβ42 Ratio Rh Bri2 BRICHOS has shown a unique ability to attenuate generation of new nucleation units by monomer dependent secondary nucleation events, which potentially can convert to neurotoxic Aβ42 oligomers during in vitro fibril formation. Further, rh Bri2 BRICHOS blocks Aβ42 induced reduction of γ oscillations in hippocampal slices ex vivo and has emerged as a model compound in molecular studies of Aβ42 fibrillation. In order to investigate whether the treatment effects now observed after rh Bri2 BRICHOS R221E administration in vivo can be mediated by the molecular mechanisms determined for BRICHOS in vitro, we asked if there is a quantitative agreement between the degrees of reduction of generation of Aβ42 oligomers, in terms of attenuation of new nucleation units, and reduction of Aβ42 induced deterioration of γ oscillations by rh Bri2 BRICHOS R221E measured in vitro and ex vivo, respectively, and the effects seen here in App$^{NL-F}$ mice.

To this end, we estimated the amounts of rh Bri2 BRICHOS R221E in the brains of the treated App$^{NL-F}$ mice from the extent of BBB passage of wildtype rh Bri2 BRICHOS measured in wildtype mice [Tambaro et al., J Biol Chem. 294, 2606-2615 (2019)] and used the measured levels of Aβ42 in App$^{NL-F}$ brain homogenates to determine the potential in vivo rh Bri2 BRICHOS R221E/Aβ42 ratio. We then estimated, using previously published data [Chen et al., Nat. Commun. 8, 2081, (2017); Chen, et al. Commun Biol. 3, 32 (2020)], what degrees of reduction of nucleation unit generation in vitro and lowering of Aβ42 induced effects on γ oscillations in hippocampal slices ex vivo, respectively, this rh Bri2 BRICHOS R221E/Aβ42 ratio corresponds to. Remarkably, the predicted reduction of oligomer generation in vitro and lowering of Aβ42 mediated neurotoxicity ex vivo that correspond to the estimated in vivo rh Bri2 BRICHOS R221E/Aβ42 ratio agree well with the reductions of Aβ positive and Thioflavin S positive plaques, GFAP staining, Iba1 levels in cortex by western blots, as well as increased physical activity observed in App$^{NL-F}$ mice after rh Bri2 BRICHOS R221E. For the degree of colocalization of Aβ and GFAP staining as well as Iba1 staining, the reductions in vivo are seemingly more pronounced than expected from the in vitro data, which possibly is related to that amplifying cascades are involved in astroglial and microglial activation in vivo.

CONCLUSIONS

Our results show that physical activity, Aβ plaque burden and astrocyte and microglia activation in App$^{NL-F}$ knock-in mice can be significantly improved by intravenous administration of rh Bri2 BRICHOS R221E.

In particular, our results support that generation of new nucleation units by surface-catalyzed secondary nucleation pathways can cause toxic effects, as indicated by the Aβ induced astrocyte and microglia activation observed in App$^{NL-F}$ mice, and that intravenous treatment with rh Bri2 BRICHOS R221E efficiently reduces neurotoxic pathways in vivo.

Our observations support that intravenous treatment of App$^{NL-F}$ knock-in mice with rh Bri2 BRICHOS R221E affects both Aβ antibody and Thioflavin S positive plaques and results in reduced activation of astrocytes as well as microglia.

The invention claimed is:

1. An isolated protein comprising a moiety of 90-200 amino acid residues having at least 70% identity to SEQ ID NO: 7, wherein the amino acid residue corresponding to position 221 in SEQ ID NO: 1 is selected from the group consisting of Glu and Asp.

2. The isolated protein according to claim 1, wherein the amino acid residue corresponding to position 221 in SEQ ID NO: 1 is Glu.

3. The isolated protein according to claim 1, wherein the moiety has at least 80% identity to SEQ ID NO: 7.

4. The isolated protein according to claim 1, consisting of not more than 500 amino acid residues.

5. The isolated protein according to claim 1, which has the amino acid sequence of SEQ ID NO: 4 or the amino acid sequence of SEQ ID NO: 13.

6. The isolated protein according to claim 1, wherein the moiety has at least 90% identity to SEQ ID NO: 7.

7. The isolated protein according to claim 1, wherein the moiety has at least 95% identity to SEQ ID NO: 7.

8. The isolated protein according to claim 1, wherein the moiety comprises the amino acid sequence of SEQ ID NO: 7, with the exception that the amino acid residue corresponding to position 221 in SEQ ID NO: 1 is selected from the group consisting of Glu and Asp.

9. A pharmaceutical composition comprising a therapeutically effective amount of the isolated protein according to claim 1 and a pharmaceutical carrier.

10. A nucleic acid comprising a sequence encoding the isolated protein according to claim 1.

* * * * *

SEQUENCE LISTING

```
<160> NUMBER OF SEQ ID NOS: 16

<210> SEQ ID NO 1
<211> LENGTH: 266
<212> TYPE: PRT
<213> ORGANISM: Homo sapiens

<400> SEQUENCE: 1

Met Val Lys Val Thr Phe Asn Ser Ala Leu Ala Gln Lys Glu Ala Lys
1               5                   10                  15

Lys Asp Glu Pro Lys Ser Gly Glu Glu Ala Leu Ile Ile Pro Pro Asp
            20                  25                  30

Ala Val Ala Val Asp Cys Lys Asp Pro Asp Asp Val Val Pro Val Gly
        35                  40                  45

Gln Arg Arg Ala Trp Cys Trp Cys Met Cys Phe Gly Leu Ala Phe Met
    50                  55                  60

Leu Ala Gly Val Ile Leu Gly Gly Ala Tyr Leu Tyr Lys Tyr Phe Ala
65                  70                  75                  80

Leu Gln Pro Asp Asp Val Tyr Tyr Cys Gly Ile Lys Tyr Ile Lys Asp
                85                  90                  95

Asp Val Ile Leu Asn Glu Pro Ser Ala Asp Ala Pro Ala Ala Leu Tyr
            100                 105                 110

Gln Thr Ile Glu Glu Asn Ile Lys Ile Phe Glu Glu Glu Glu Val Glu
            115                 120                 125

Phe Ile Ser Val Pro Val Pro Glu Phe Ala Asp Ser Asp Pro Ala Asn
    130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
                165                 170                 175

Pro Arg Asn Leu Leu Glu Leu Leu Ile Asn Ile Lys Ala Gly Thr Tyr
                180                 185                 190

Leu Pro Gln Ser Tyr Leu Ile His Glu His Met Val Ile Thr Asp Arg
            195                 200                 205

Ile Glu Asn Ile Asp His Leu Gly Phe Phe Ile Tyr Arg Leu Cys His
    210                 215                 220

Asp Lys Glu Thr Tyr Lys Leu Gln Arg Arg Glu Thr Ile Lys Gly Ile
225                 230                 235                 240

Gln Lys Arg Glu Ala Ser Asn Cys Phe Ala Ile Arg His Phe Glu Asn
                245                 250                 255

Lys Phe Ala Val Glu Thr Leu Ile Cys Ser
                260                 265

<210> SEQ ID NO 2
```

-continued

```
<211> LENGTH: 270
<212> TYPE: PRT
<213> ORGANISM: Artificial Sequence
<220> FEATURE:
<223> OTHER INFORMATION: mutant

<400> SEQUENCE: 2

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
            35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
    130                 135                 140

Ser Leu Val Pro Arg Gly Ser Gln Thr Ile Glu Glu Asn Ile Lys Ile
145                 150                 155                 160

Phe Glu Glu Glu Glu Val Glu Phe Ile Ser Val Pro Val Pro Glu Phe
                165                 170                 175

Ala Asp Ser Asp Pro Ala Asn Ile Val His Asp Phe Asn Lys Lys Leu
            180                 185                 190

Thr Ala Tyr Leu Asp Leu Asn Leu Asp Lys Cys Tyr Val Ile Pro Leu
            195                 200                 205

Asn Thr Ser Ile Val Met Pro Pro Arg Asn Leu Leu Glu Leu Leu Ile
    210                 215                 220

Asn Ile Lys Ala Gly Thr Tyr Leu Pro Gln Ser Tyr Leu Ile His Glu
225                 230                 235                 240

His Met Val Ile Thr Asp Arg Ile Glu Asn Ile Asp His Leu Gly Phe
                245                 250                 255

Phe Ile Tyr Glu Leu Cys His Asp Lys Glu Thr Tyr Lys Leu
            260                 265                 270

<210> SEQ ID NO 3
<211> LENGTH: 119
<212> TYPE: PRT
<213> ORGANISM: Homo sapiens

<400> SEQUENCE: 3

Gln Thr Ile Glu Glu Asn Ile Lys Ile Phe Glu Glu Glu Glu Val Glu
1               5                   10                  15

Phe Ile Ser Val Pro Val Pro Glu Phe Ala Asp Ser Asp Pro Ala Asn
            20                  25                  30

Ile Val His Asp Phe Asn Lys Lys Leu Thr Ala Tyr Leu Asp Leu Asn
            35                  40                  45

Leu Asp Lys Cys Tyr Val Ile Pro Leu Asn Thr Ser Ile Val Met Pro
    50                  55                  60
```

-continued

```
Pro Arg Asn Leu Leu Glu Leu Leu Ile Asn Ile Lys Ala Gly Thr Tyr
65                  70              75                  80

Leu Pro Gln Ser Tyr Leu Ile His Glu His Met Val Ile Thr Asp Arg
                85                  90                  95

Ile Glu Asn Ile Asp His Leu Gly Phe Phe Ile Tyr Arg Leu Cys His
                100             105             110

Asp Lys Glu Thr Tyr Lys Leu
        115
```

<210> SEQ ID NO 4
<211> LENGTH: 119
<212> TYPE: PRT
<213> ORGANISM: Artificial Sequence
<220> FEATURE:
<223> OTHER INFORMATION: mutant

<400> SEQUENCE: 4

```
Gln Thr Ile Glu Glu Asn Ile Lys Ile Phe Glu Glu Glu Val Glu
1               5               10                  15

Phe Ile Ser Val Pro Val Pro Glu Phe Ala Asp Ser Asp Pro Ala Asn
                20              25              30

Ile Val His Asp Phe Asn Lys Lys Leu Thr Ala Tyr Leu Asp Leu Asn
        35              40                  45

Leu Asp Lys Cys Tyr Val Ile Pro Leu Asn Thr Ser Ile Val Met Pro
    50              55              60

Pro Arg Asn Leu Leu Glu Leu Leu Ile Asn Ile Lys Ala Gly Thr Tyr
65                  70              75                  80

Leu Pro Gln Ser Tyr Leu Ile His Glu His Met Val Ile Thr Asp Arg
                85                  90                  95

Ile Glu Asn Ile Asp His Leu Gly Phe Phe Ile Tyr Glu Leu Cys His
                100             105             110

Asp Lys Glu Thr Tyr Lys Leu
        115
```

<210> SEQ ID NO 5
<211> LENGTH: 89
<212> TYPE: PRT
<213> ORGANISM: Homo sapiens

<400> SEQUENCE: 5

```
Met Val Lys Val Thr Phe Asn Ser Ala Leu Ala Gln Lys Glu Ala Lys
1               5               10                  15

Lys Asp Glu Pro Lys Ser Gly Glu Glu Ala Leu Ile Ile Pro Pro Asp
                20              25              30

Ala Val Ala Val Asp Cys Lys Asp Pro Asp Asp Val Val Pro Val Gly
        35              40                  45

Gln Arg Arg Ala Trp Cys Trp Cys Met Cys Phe Gly Leu Ala Phe Met
    50              55              60

Leu Ala Gly Val Ile Leu Gly Gly Ala Tyr Leu Tyr Lys Tyr Phe Ala
65                  70              75                  80

Leu Gln Pro Asp Asp Val Tyr Tyr Cys
                85
```

<210> SEQ ID NO 6
<211> LENGTH: 23
<212> TYPE: PRT
<213> ORGANISM: Homo sapiens

<400> SEQUENCE: 6

-continued

Glu Ala Ser Asn Cys Phe Ala Ile Arg His Phe Glu Asn Lys Phe Ala
1               5                   10                  15

Val Glu Thr Leu Ile Cys Ser
            20

<210> SEQ ID NO 7
<211> LENGTH: 95
<212> TYPE: PRT
<213> ORGANISM: Homo sapiens

<400> SEQUENCE: 7

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
            20                  25                  30

Leu Asn Thr Ser Ile Val Met Pro Pro Arg Asn Leu Leu Glu Leu Leu
            35                  40                  45

Ile Asn Ile Lys Ala Gly Thr Tyr Leu Pro Gln Ser Tyr Leu Ile His
        50                  55                  60

Glu His Met Val Ile Thr Asp Arg Ile Glu Asn Ile Asp His Leu Gly
65                  70                  75                  80

Phe Phe Ile Tyr Arg Leu Cys His Asp Lys Glu Thr Tyr Lys Leu
                85                  90                  95

<210> SEQ ID NO 8
<211> LENGTH: 95
<212> TYPE: PRT
<213> ORGANISM: Pan troglodytes

<400> SEQUENCE: 8

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
            20                  25                  30

Leu Asn Thr Ser Ile Val Met Pro Pro Arg Asn Leu Leu Glu Leu Leu
            35                  40                  45

Ile Asn Ile Lys Ala Gly Thr Tyr Leu Pro Gln Ser Tyr Leu Ile His
        50                  55                  60

Glu His Met Val Ile Thr Asp Arg Ile Glu Asn Ile Asp His Leu Gly
65                  70                  75                  80

Phe Phe Ile Tyr Arg Leu Cys His Asp Lys Glu Thr Tyr Lys Leu
                85                  90                  95

<210> SEQ ID NO 9
<211> LENGTH: 95
<212> TYPE: PRT
<213> ORGANISM: Bos taurus

<400> SEQUENCE: 9

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
            20                  25                  30

Leu Asn Thr Ser Ile Val Met Pro Pro Lys Asn Leu Leu Glu Leu Leu
            35                  40                  45

Ile Asn Ile Lys Ala Gly Thr Tyr Leu Pro Gln Ser Tyr Leu Ile His
        50                  55                  60

-continued

```
Glu His Met Val Ile Thr Asp Arg Ile Glu Asn Ile Asp His Leu Gly
65                  70                  75                  80

Phe Tyr Ile Tyr Arg Leu Cys His Asp Lys Glu Thr Tyr Lys Leu
                85                  90                  95

<210> SEQ ID NO 10
<211> LENGTH: 95
<212> TYPE: PRT
<213> ORGANISM: Sus scrofa

<400> SEQUENCE: 10

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
                20                  25                  30

Leu Asn Thr Ser Ile Val Met Pro Pro Arg Asn Leu Leu Glu Leu Leu
            35                  40                  45

Ile Asn Ile Lys Ala Gly Thr Tyr Leu Pro Gln Ser Tyr Leu Ile His
        50                  55                  60

Glu His Met Val Ile Thr Asp Arg Ile Glu Asn Ile Asp His Leu Gly
65                  70                  75                  80

Phe Tyr Ile Tyr Arg Leu Cys His Asp Lys Glu Thr Tyr Lys Leu
                85                  90                  95

<210> SEQ ID NO 11
<211> LENGTH: 95
<212> TYPE: PRT
<213> ORGANISM: Mus musculus

<400> SEQUENCE: 11

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
                20                  25                  30

Leu Asn Thr Ser Ile Val Met Pro Pro Lys Asn Leu Leu Glu Leu Leu
            35                  40                  45

Ile Asn Ile Lys Ala Gly Thr Tyr Leu Pro Gln Ser Tyr Leu Ile His
        50                  55                  60

Glu His Met Val Ile Thr Asp Arg Ile Glu Asn Val Asp Asn Leu Gly
65                  70                  75                  80

Phe Phe Ile Tyr Arg Leu Cys His Asp Lys Glu Thr Tyr Lys Leu
                85                  90                  95

<210> SEQ ID NO 12
<211> LENGTH: 95
<212> TYPE: PRT
<213> ORGANISM: Rattus norvegicus

<400> SEQUENCE: 12

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
                20                  25                  30

Leu Asn Thr Ser Ile Val Met Pro Pro Arg Asn Leu Leu Glu Leu Leu
            35                  40                  45

Ile Asn Ile Lys Ala Gly Thr Tyr Leu Pro Gln Ser Tyr Leu Ile His
        50                  55                  60

Glu His Met Val Ile Thr Asp Arg Ile Glu Asn Val Asp His Leu Gly
```

```
65                70               75                80

Phe Phe Ile Tyr Arg Leu Cys His Asp Lys Glu Thr Tyr Lys Leu
                85                90                95

<210> SEQ ID NO 13
<211> LENGTH: 95
<212> TYPE: PRT
<213> ORGANISM: Artificial Sequence
<220> FEATURE:
<223> OTHER INFORMATION: mutant

<400> SEQUENCE: 13

Phe Ala Asp Ser Asp Pro Ala Asn Ile Val His Asp Phe Asn Lys Lys
1               5                10                15

Leu Thr Ala Tyr Leu Asp Leu Asn Leu Asp Lys Cys Tyr Val Ile Pro
             20                25                30

Leu Asn Thr Ser Ile Val Met Pro Pro Arg Asn Leu Leu Glu Leu Leu
          35                40                45

Ile Asn Ile Lys Ala Gly Thr Tyr Leu Pro Gln Ser Tyr Leu Ile His
       50                55                60

Glu His Met Val Ile Thr Asp Arg Ile Glu Asn Ile Asp His Leu Gly
65                70                75                80

Phe Phe Ile Tyr Glu Leu Cys His Asp Lys Glu Thr Tyr Lys Leu
                85                90                95

<210> SEQ ID NO 14
<211> LENGTH: 44
<212> TYPE: DNA
<213> ORGANISM: Homo sapiens

<400> SEQUENCE: 14
cacctgggtt tctttattta tgaactgtgt catgacaagg aaac              44

<210> SEQ ID NO 15
<211> LENGTH: 44
<212> TYPE: DNA
<213> ORGANISM: Homo sapiens

<400> SEQUENCE: 15
gtttccttgt catgacacag ttcataaata aagaaaccca ggtg              44

<210> SEQ ID NO 16
<211> LENGTH: 810
<212> TYPE: DNA
<213> ORGANISM: Artificial Sequence
<220> FEATURE:
<223> OTHER INFORMATION: mutant

<400> SEQUENCE: 16
atgggccatc atcatcatca tcatatgtca cacactacac catggacaaa cccaggactc     60
gcagaaaact tcatgaacag tttcatgcaa ggcctgagct cgatgccagg tttcacggca    120
agccaattgg ataagatgtc aaccatcgca caatccatgg tacagtcaat acaatccttg    180
gcggcacaag gcaggacatc accgaatgac ctgcaggccc ttaacatggc ttttgcatct    240
tcgatggcag aaatcgcggc atccgaagaa ggaggggaa gcctttccac caaaactagc     300
tctatagcca gtgcaatgtc caacgcgttt ctgcaaacaa ctggagtggt aaaccaaccg    360
ttcataaatg aaataactca gctcgttagc atgtttgctc aagcaggtat gaatgatgtc    420
agtgctggga attccctggt gccacgcgg tctcagacaa ttgaagaaaa tattaaaatc    480
```

-continued

```
tttgaagaag aagaagttga atttatcagt gtgcctgtcc cagagtttgc agatagtgat        540
cctgccaaca ttgttcatga ctttaacaag aaacttacag cctatttaga tcttaacctg        600
gataagtgct atgtgatccc tctgaacact tccattgtta tgccacccag aaacctactg        660
gagttactta ttaacatcaa ggctggaacc tatttgcctc agtcctatct gattcatgag        720
cacatggtta ttactgatcg cattgaaaac attgatcacc tgggtttctt tatttatgaa        780
ctgtgtcatg acaaggaaac ttacaaactg                                         810
```